US011980407B1

(12) United States Patent
Rahimzadeh et al.

(10) Patent No.: US 11,980,407 B1
(45) Date of Patent: May 14, 2024

(54) METHOD OF CRYOTHERAPY WITH AN ENDOSCOPY TUBE

(71) Applicants: Jason Rahimzadeh, Westwood, NJ (US); Paul Robert Wickern, San Antonio, TX (US)

(72) Inventors: Jason Rahimzadeh, Westwood, NJ (US); Paul Robert Wickern, San Antonio, TX (US)

( * ) Notice: Subject to any disclaimer, the term of this patent is extended or adjusted under 35 U.S.C. 154(b) by 114 days.

(21) Appl. No.: 17/559,869

(22) Filed: Dec. 22, 2021

Related U.S. Application Data

(62) Division of application No. 16/265,040, filed on Feb. 1, 2019, now Pat. No. 11,259,858.

(60) Provisional application No. 62/626,683, filed on Feb. 6, 2018.

(51) Int. Cl.
| | |
|---|---|
| *A61B 18/02* | (2006.01) |
| *A61B 1/00* | (2006.01) |
| *A61B 1/005* | (2006.01) |
| *A61B 1/015* | (2006.01) |
| *A61B 1/04* | (2006.01) |
| *A61B 1/06* | (2006.01) |
| *A61B 1/233* | (2006.01) |
| *A61B 18/00* | (2006.01) |
| *A61M 25/09* | (2006.01) |

(52) U.S. Cl.
CPC ...... *A61B 18/0218* (2013.01); *A61B 1/00082* (2013.01); *A61B 1/00091* (2013.01); *A61B 1/00131* (2013.01); *A61B 1/0057* (2013.01); *A61B 1/015* (2013.01); *A61B 1/046* (2022.02); *A61B 1/06* (2013.01); *A61B 1/233* (2013.01); *A61B 2018/00041* (2013.01); *A61B 2018/0022* (2013.01); *A61B 2018/00488* (2013.01); *A61B 2018/00982* (2013.01); *A61B 2018/0212* (2013.01); *A61M 25/09* (2013.01)

(58) Field of Classification Search
None
See application file for complete search history.

(56) References Cited

U.S. PATENT DOCUMENTS

| | | |
|---|---|---|
| 4,580,551 A | 4/1986 | Siegmund |
| 5,902,413 A | 5/1999 | Puszko et al. |
| 6,027,499 A | 6/2000 | Johnston et al. |
| 6,176,825 B1 | 1/2001 | Chin et al. |
| 6,749,560 B1 | 6/2004 | Konstorum |

(Continued)

*Primary Examiner* — John P Leubecker
(74) *Attorney, Agent, or Firm* — Edward S. Sherman, Esq.; Alan Heimlich

(57) ABSTRACT

An endoscopy device is configured with a flexible cannula or tube for nasal insertion and has multiple parallel and adjacent lumens that provide sub-chambers configured to provide means to diagnose and treat Barrett's esophagus, such as by spray cryo-therapy with no further insertion of tubes. The lumens are configured to impart a small diameter with sufficient flexibility for nasal insertion into a patient's esophagus and accommodate a means any treatment modality. In the case of cryo-therapy, a lumen provides gas pressure relief, and is along the tube, with separate lumens for the delivery of a liquid freezing agent and an imaging means, which includes a source of illumination. Outer lumens may support guide wires used to steer the tube tip and aim the camera to determine the where to immobilize tip before the start of the treatment and/or to correct strictures formed in prior procedures.

7 Claims, 24 Drawing Sheets

(56) References Cited

U.S. PATENT DOCUMENTS

| | | |
|---|---|---|
| 6,840,909 B2 | 1/2005 | Gatto |
| 2004/0249246 A1 | 12/2004 | Campos |
| 2005/0059862 A1 | 3/2005 | Phan |
| 2005/0085692 A1 | 4/2005 | Kiehn |
| 2005/0203341 A1 | 9/2005 | Welker |
| 2005/0240147 A1 | 10/2005 | Makower |
| 2005/0272975 A1 | 12/2005 | McWeeney |
| 2007/0083084 A1 | 4/2007 | Esahi |
| 2007/0276360 A1 | 11/2007 | Johnston et al. |
| 2009/0062871 A1 | 3/2009 | Chin |
| 2011/0196302 A1 | 8/2011 | Gildersleeve et al. |
| 2011/0208166 A1 | 8/2011 | Dumot et al. |
| 2011/0218493 A1* | 9/2011 | Miyasaka ............. A61J 15/003 604/96.01 |
| 2012/0095292 A1 | 4/2012 | Gunday |
| 2012/0136343 A1* | 5/2012 | Burnett ................. A61M 25/10 606/27 |
| 2012/0197245 A1* | 8/2012 | Burnett ............ A61B 17/12022 606/21 |
| 2013/0073015 A1* | 3/2013 | Rozenberg ........ A61M 25/0068 607/105 |
| 2013/0231651 A1 | 9/2013 | Burr et al. |
| 2015/0066005 A1 | 3/2015 | Fan et al. |
| 2016/0174819 A1 | 6/2016 | Ouyang |
| 2017/0042618 A1 | 2/2017 | Brown |
| 2017/0311789 A1 | 11/2017 | Mulcahey |
| 2018/0014868 A1* | 1/2018 | O'Connor .......... A61B 18/0218 |
| 2018/0200416 A1* | 7/2018 | Oza ...................... A61B 1/2733 |
| 2019/0380761 A1* | 12/2019 | Catanzaro ................ A61F 7/123 |
| 2020/0297403 A1* | 9/2020 | Kochavi ................ A61B 1/126 |
| 2023/0037101 A1* | 2/2023 | Kashintsev ........ A61M 25/1011 |

\* cited by examiner

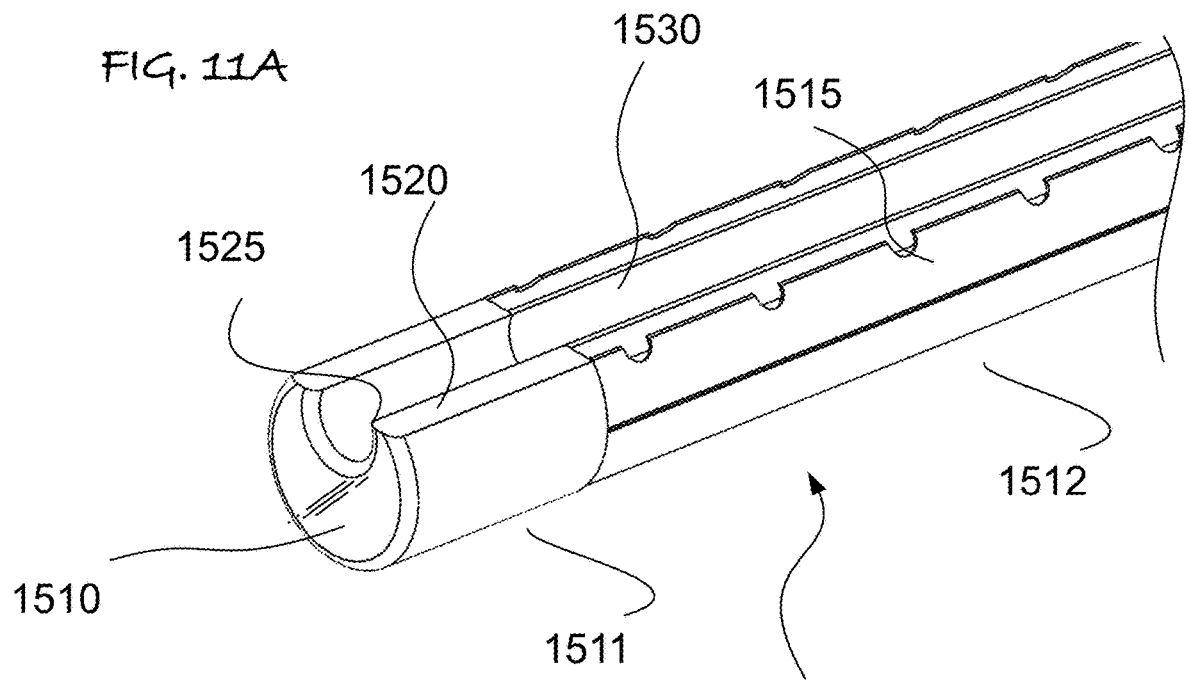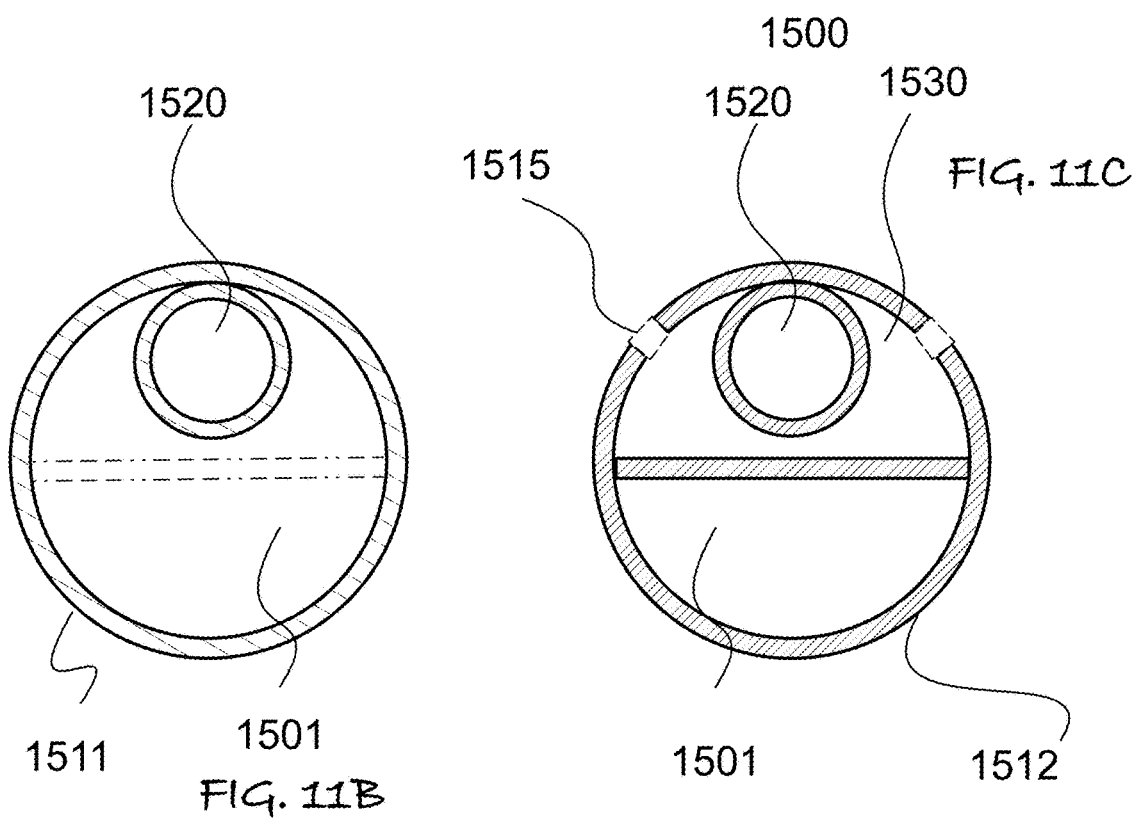

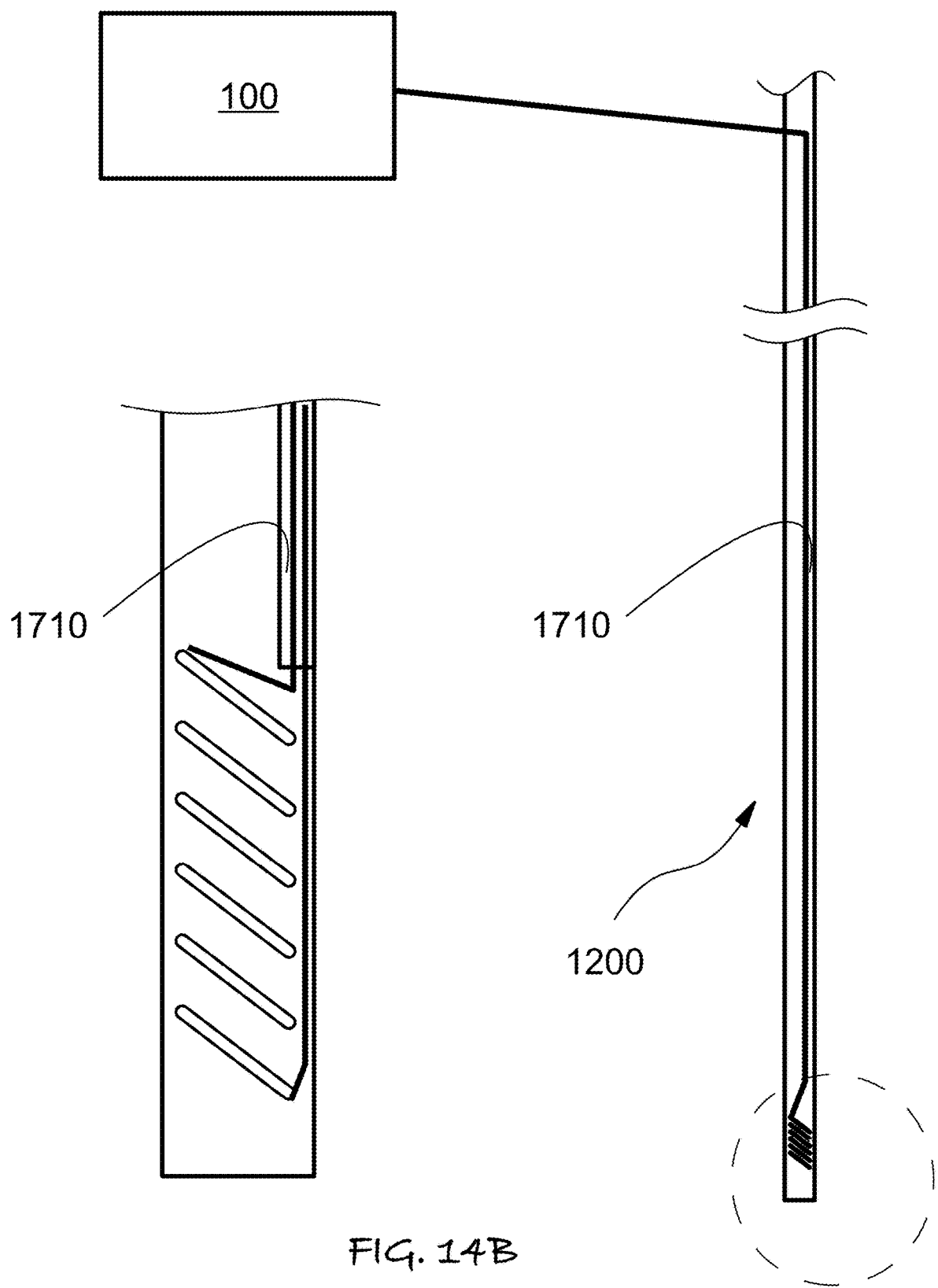

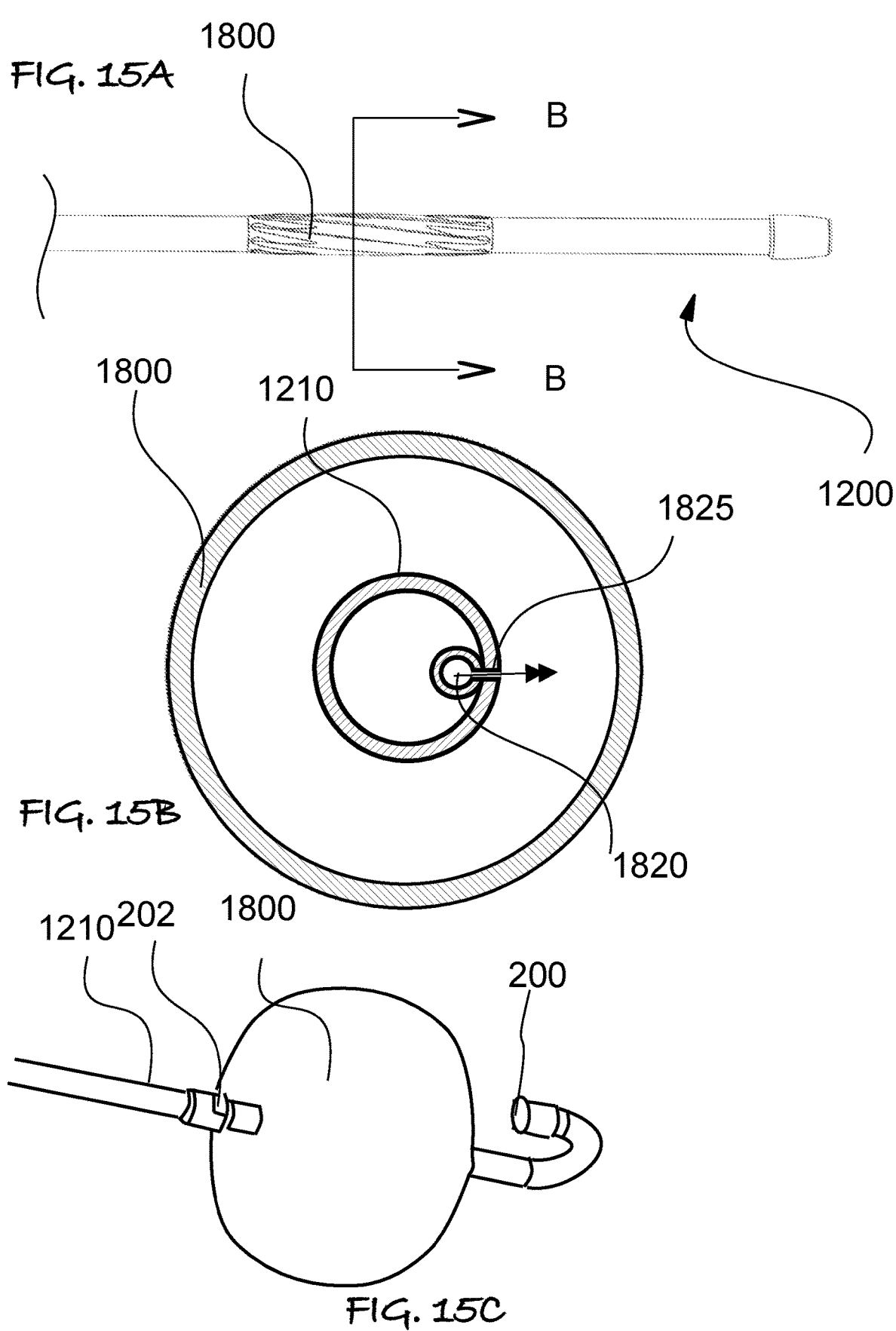

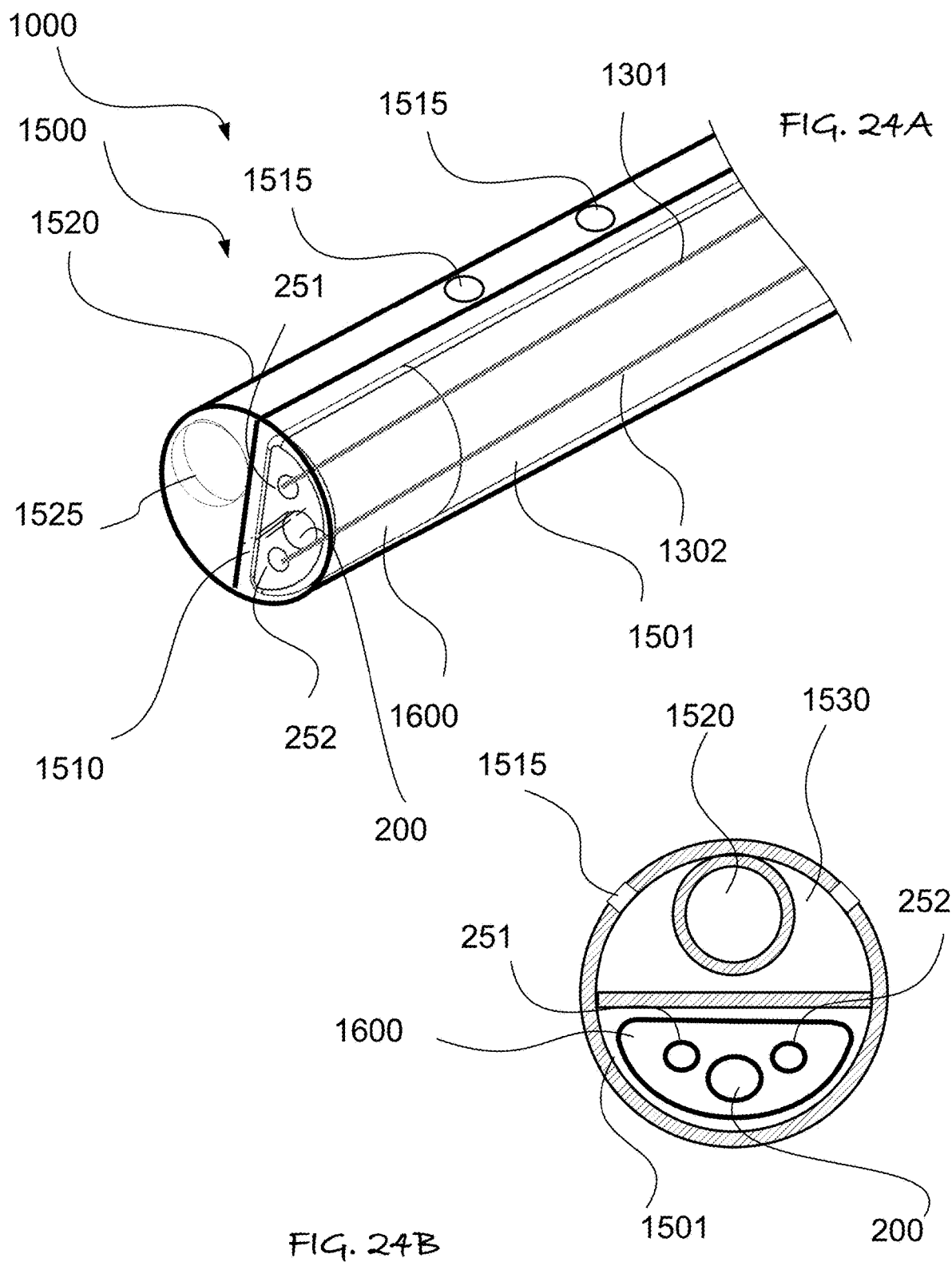

METHOD OF CRYOTHERAPY WITH AN ENDOSCOPY TUBE

CROSS REFERENCE TO RELATED APPLICATIONS

The present application is a Division of and claims the benefit of priority to the Non-provisional application for an "ENDOSCOPY DEVICE AND METHOD" that was filed on Feb. 1, 2019, having application Ser. No. 16/265,040, now U.S. Pat. No. 11,259,858 issued Mar. 1, 2022 which is incorporated herein by reference.

The present application also claims the benefit of priority to the US Provisional patent application for an "ENDOSCOPY DEVICE AND METHOD" that was filed on Feb. 6, 2018, having application Ser. No. 62/626,683 and is incorporated herein by reference.

BACKGROUND OF INVENTION

The field of inventions is endoscopes and related catheter devices, and more specifically such endoscopes configured for treatment of various medical conditions.

Endoscopes are well known in the art for diagnostic, treatment and surgical purposes.

Depending on the route of entry and the need for surgical incisions to create entry routes other than natural body cavities, a treatment may require sedation to keep the patient still an/or avoid pain and discomfort. Endoscopes generally refer to tubular and catheter type devices that are inserted via natural body cavities, whereas similar devices inserted through surgical opening are generally referred to as laparoscopes.

It would be advantageous to perform many procedures without sedation in a clinic, but rather in the office of the treating physician to save both patient and physician time and reduce costs.

Sterilization of endoscopes and catheters, tubes and lumens they deploy is a barrier to office treatment, requiring special equipment and multiple devices.

Some treatment modalities use multiple catheters and a single endoscope for finding and viewing the tissue of interest for treatment, adding to the complexity of treatment, and the need for multiple sterile devices on hand.

According it has been recognized that there are multiple barriers to enabling more in office treatments.

Accordingly, it is an object of the invention to provide for endoscopic procedures without a needs for sterilization by configuring the catheters, tubes and lumens associated therewith so that they can be made at least partially disposable in a compact form that is easy for the treating physician to manipulate.

The above and other objects, effects, features, and advantages of the present invention will become more apparent from the following description of the embodiments thereof taken in conjunction with the accompanying drawings

SUMMARY OF INVENTION

In the present invention, the first object is achieved by providing a flexible tubular member for endoscopic procedures, the member comprising: a tube having a proximal end and an opposing distal end with an outer wall extending between the ends, the tube having an outer diameter of less than about 10 mm, multiple parallel lumens that extend generally between the proximal and distal ends of the tube, including; at least one lumen having a plurality of perforations through the outer wall adjacent the distal end of the tube, a pair of guide wires disposed to extend from about the distal end of the tube to the proximal end of the tube, two or more remaining lumens for an imaging means and a fluid spray means.

A second aspect of the invention is characterized by such a flexible tubular member for endoscopic procedures that is further comprising an inflation fixation means disposed at least about 10 mm from the distal end of the tube.

Another aspect of the invention is characterized by any such flexible tubular member for endoscopic procedures wherein the multiple parallel lumens that extend generally between the proximal and distal ends of the tube, include; a first central lumen with a bore of a first diameter that disposed within a ovoid member, the ovoid member being connected at a top and bottom to the outer wall of the tube, a second central lumen with a bore of a second diameter that is smaller than the first diameter, the second lumen being disposed within the ovoid member and adjacent to the first central member, wherein the at least one lumen having a plurality of perforations through the outer wall adjacent the distal end of the tube comprises a pair of generally lobe shaped elongated lumens, each being disposed between opposing side of the outer wall of the tube and an adjacent side of the ovoid member, one of said pair being the first lumen having a plurality of perforations through the outer wall adjacent the distal end of the tube, and the other of the pair being an additional lumen having a plurality of perforations through the outer wall adjacent the distal end of the tube.

Another aspect of the invention is characterized by any such flexible tubular member for endoscopic procedures wherein each of the guide wires of the pair are disposed in an opposite side of the outer wall of the tube adjacent each of the lobe shaped elongated lumens in which each guide wire is surround by tube outer wall such that an inner portion of the tube wall projects as a protuberance into each of the generally lobe shaped elongated lumens to narrow the width of each of the generally lobe shaped elongated lumens adjacent the guide wire in the tube wall.

Another aspect of the invention is characterized by any such flexible tubular member for endoscopic procedures wherein the first central lumen has a discharge portal adjacent the distal end of the tube and a receiving portal at the proximal end of the tube.

Another aspect of the invention is characterized by any such flexible tubular member for endoscopic procedures that has a length of at least about 55 cm.

Another aspect of the invention is characterized by any such flexible tubular member for endoscopic procedures that has a length of less than about 115 cm.

Another aspect of the invention is characterized by any such flexible tubular member for endoscopic procedures wherein the tube is an outer sheath and the lumen for imaging is a sealed lumen of the outer sheath, the sealed lumen having an optically transparent window at the distal end of the tube in which the guide wires are coupled to the imaging means and co-disposed in the sealed lumen, and the sheath provides the pair of the first and a second lumen and the lumen for the fluid spray means.

Another aspect of the invention is characterized by any such flexible tubular member for endoscopic procedures that has an outer diameter of less than about 10 mm.

Another aspect of the invention is characterized by any such flexible tubular member for endoscopic procedures wherein the one of the two or more remaining lumen is configured to provide the fluid spray means and has an interior cross-sectional area transverse to the lumen of at least about 6 mm$^2$.

Another aspect of the invention is characterized by any such flexible tubular member for endoscopic procedures wherein the lumen for the fluid spray means comprises a heating means.

Another aspect of the invention is characterized by any such flexible tubular member for endoscopic procedures wherein the plurality of perforations through the outer wall adjacent of the tube are disposed between the inflation fixation means and the distal end of the tube.

Another aspect of the invention is characterized by a method of treating a patient comprising the steps of providing a flexible tube having; a proximal end and an opposing distal ends with an outer wall extending between the ends, multiple parallel lumens that extend generally between the proximal and distal ends of the flexible tube, including at least a first lumen adjacent the outer wall of the flexible tube, a plurality of perforation in the outer wall of the flexible tube that penetrate to the first lumen, wherein the first lumen has an upper vent portal adjacent the proximal end, providing a patient, introducing the distal end of the flexible tube through the nose of the patient into a nasal cavity, advancing the flexible tube from the nasal cavity into the esophagus, identifying an area of the esophagus to be treated, fixing the flexible tube such that the distal end of the tube is disposed adjacent to the area to be treated, introducing a liquid freezing agent into the proximal end of the tube for delivery via at least one of the multiple parallel lumen to exit a fluid spray means at the distal end of the tube, whereas a gaseous form of the liquid freezing agent that expands on warming can flow toward the proximal end of the tube via by entering the first lumen via the plurality of perforations therein.

Another aspect of the invention is characterized by such a method of treating a patient wherein the at least one of the multiple parallel lumens is provided as an exit for the fluid spray means at the distal end of the tube that has a heating means.

Another aspect of the invention is characterized by any such method of treating a patient wherein the plurality of perforations through the outer wall of the tube that penetrate to the first lumen are disposed between the inflation fixation means and the distal end of the tube.

Another aspect of the invention is characterized by a method of using an endoscopy tube comprising the steps of preparing an endoscopy device by; providing a tubular member comprising; a tube having a proximal end and an opposing distal ends with an outer wall extending between the ends, multiple parallel lumens that extend generally between the proximal and distal ends of the tube, including at least a first lumen adjacent the outer wall of the tube, a plurality of perforation in the outer wall of the tube that penetrate to the first lumen, wherein the first lumen has an upper vent portal adjacent the proximal end, a second lumen that is open at a proximal end and closed at a distal end and having an optically transparent window at the distal end of the tube, a third lumen open at the proximal end and the distal end for transporting a liquid freezing agent to a region to be treated, providing an endoscopy tube having; a steering means, an imaging means disposed at the distal end of the endoscopy tube, and an illumination means disposed at the distal end of the endoscopy tube, inserting the distal end of the end of the endoscopy tube within the second lumen of the tubular member at the open proximal end, advancing the distal end of the endoscopy tube within the second lumen toward the distal end of the second lumen to dispose the imaging and illumination means adjacent to the optically transparent window for illuminating and obtaining images of tissues exterior to the tubular member and the tubular member covers the endoscopy tube, wherein said step of advancing provides a covered endoscopy tube, inserting the covered endoscopy tube in a body cavity of a patient, performing a treatment procedure that includes applying a quantity of liquid freezing agent to an area to be treated and obtaining images of the area to be treated at least after the treatment is performed, removing the covered endoscopy tube from the body cavity, removing the tubular member from the endoscopy tube, disposing of the tubular member.

Another aspect of the invention is characterized by such a method of using an endoscopy tube wherein the covered endoscopy tube is inserted into a body cavity of a patient from the nasal cavity of the patient and the body cavity is the esophagus.

Another aspect of the invention is characterized by any such method of using an endoscopy tube wherein the covered endoscopy tube is inserted into a body cavity of a patient from the mouth of the patient and the body cavity is at least one lung.

Another aspect of the invention is characterized by any such method of using an endoscopy tube wherein the third lumen comprises a heating means.

Another aspect of the invention is characterized by any such method of using an endoscopy tube wherein the interior of the third lumen has a cross-sectional area transverse to the lumen of at least about 6 mm$^2$.

The above and other objects, effects, features, and advantages of the present invention will become more apparent from the following description of the embodiments thereof taken in conjunction with the accompanying drawings.

BRIEF DESCRIPTION OF DRAWINGS

FIG. 3A is perspective view of the distal end of another embodiment of the endoscope showing a balloon in a collapsed state, whereas

FIG. 11A is isometric cut-away view of the embodiment of the sheath in FIG. 10 and FIGS. 11B and 11C are transverse section views of different portions thereof.

FIG. 13A is an isometric view of another embodiment of the invention in which a heating element is disposed within the tube of FIG. 4-5 at the tip, whereas

FIG. 14A is a schematic diagram showing an electrical connection of the heater element to the controller, whereas FIG. 14B is an enlarged view of the distal end of the tube showing the connection of wiring to the heater element.

FIG. 15A is an external elevation of the portion of the catheter tube with the fixation and expansion means; FIG. 15B is a transverse sectional elevation at section line B-B when the balloon portion in FIG. 15A is inflated, as shown in the perspective view in FIG. 15C.

FIG. 16A is a longitudinal sectional view of the inflated balloon in FIG. 15A-C, wherein

FIG. 17A is isometric view of another embodiment of the invention in which a second imaging means is disposed in a position to the view the imaging means at the distal and the balloon member, whereas

FIG. 22A is an exploded isometric view of another embodiment of the invention showing the applicator tip and end portion for the connected tube, whereas FIG. 22B is a transverse section of the tube at section line B-B in FIG. 22A.

FIG. 24A is a transparent perspective view of the sheath including the inserted "D" shaped member and FIG. 24B is transverse section view at the interface of the permanent member and the lumen of the sheath containing it and the guidewires.

DETAILED DESCRIPTION

Figure 1:
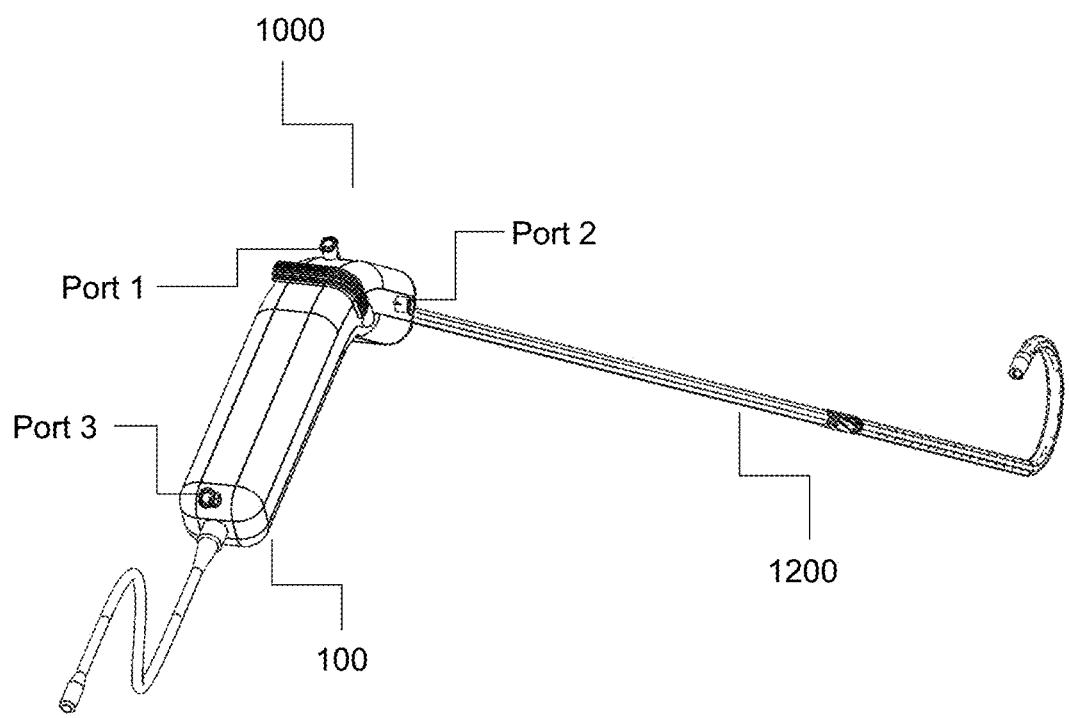
FIG. 1 is a schematic perspective view of an endoscope and controller
Figure 2:
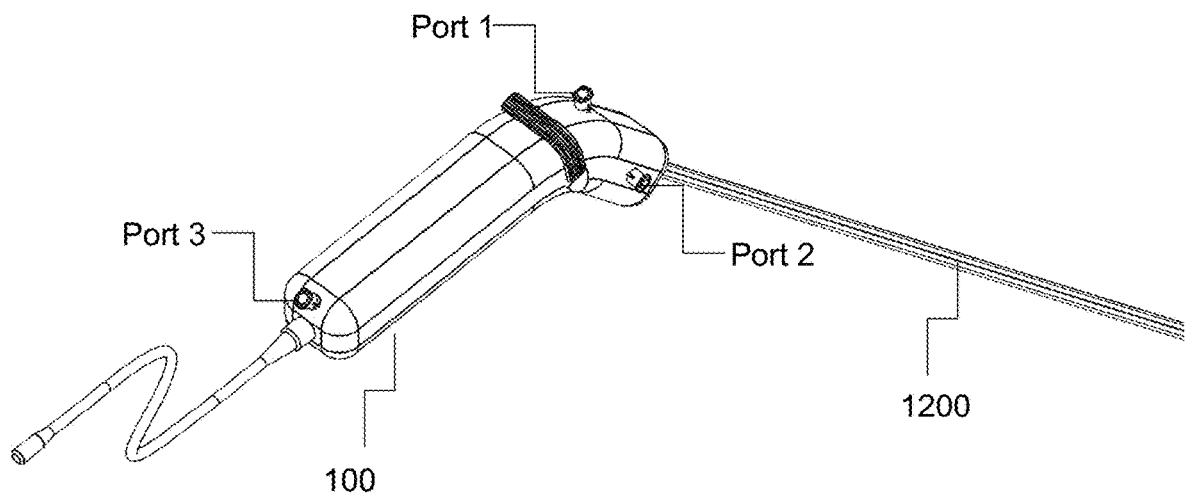
FIG. 2 is another perspective view of the endoscope and controller in FIG. 1.
Figure 3A:
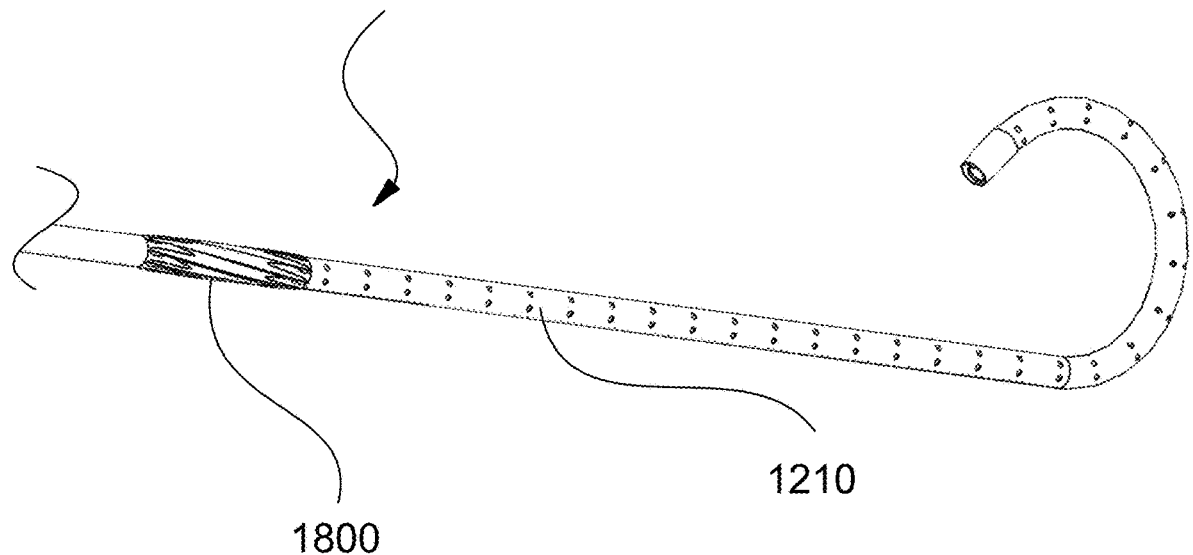
Figure 3B:
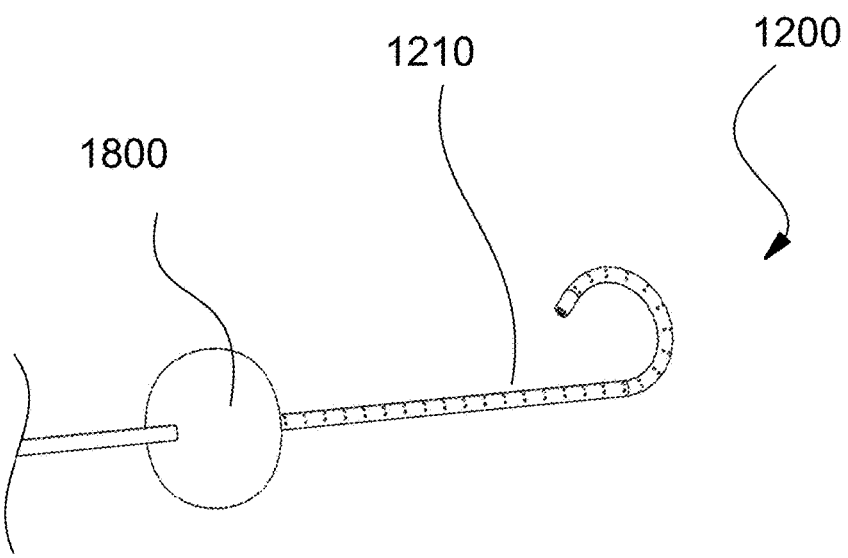
FIG. 3B illustrates the balloon in an inflated state.

Referring to FIGS. 1 through 24B, wherein like reference numerals refer to like components in the various views, there is illustrated therein a new and improved endoscopy device, generally denominated 1000 herein.

It should be apparent from the foregoing that the devices according to the various embodiments will provide the benefits allowing treating physicians to provide office-based treatment of patients without sedation, as for example when the device or portion thereof are disposable, and sterilization is avoided, and also when the diameter coupled with the flexible nature permits entry through the nasal passages in the esophagus. Such devices can lower total cost treatment method by avoiding the cost and facility for general anesthesia. In certain embodiments, the use of disposable sheath to cover a re-usable device saves costs. Further, the physicians ease of use will be enhanced with only a single catheter to manipulate vs. multiple catheters/instruments that may need to be separately sterilized and provided by an assistant.

It should be understood that an endoscope is in essence an external control device for manipulating one or more aspects of a catheter for insertion in a natural body cavity or surgical body opening and viewing an aspect of tissues prior to or during a contemplated medical procedure.

A contemplated use of various embodiment of the invention are for cryotherapeutic treatment of Barrett's esophagus, which involves the controlled application of a liquid freezing agent, usually liquid nitrogen, to selected tissue visualized with an endoscope. Conventionally, the treatment is done by introducing the catheter end of the endoscope orally, identify the tissue needing treatment, and introducing additional catheters to locally introduce the liquid nitrogen, as well as capture and direct the expanding gas from the heated liquid treatment region of the patient.

The improvement in various embodiments that follow will enable treatment without sedation in an office environment by using one of more disposable components in generally a single endoscope device. The preferred embodiments of such catheters are configured for nasal entry. According, in various embodiments the total outer diameter of the tube is less than about 10 mm, but preferably less than about 8 mm and more preferably less than about 6 mm for nasal entry.

In accordance with the present invention the endoscopy device 1000 comprises a controller 100 and a coupled catheter member 1200 formed of a tube 1210 with an outer wall 1211, multiple parallel lumens 1220 including at least a first lumen 1221 adjacent the outer wall 1211 of the tube 1210. The first lumen 1210 is optionally open via portal 1217 at the distal end of the tube and the proximal end in communication with the controller for the controlled introduction of tools or materials. A plurality of perforation 1215 in the wall 1211 of the tube 1210 that penetrate to the first lumen 1221. With reference to the distal end of the catheter member 1200 most distal from the controller 1100 device, the first lumen 1221 may extend upward to release gas adjacent the proximal end of the tube outside of a patient. It should also be appreciated that multiple parallel lumens 1220 may including at least a first lumen 1221 adjacent the outer wall 1211 of the tube 1210. The controller 100 may have one, two or three external ports in communications with the various lumens, such as for inserting tools, releasing gas formed in or from a cryo-treatment, as well as inserting a fluid, either as a gas or liquid into a lumen.

Figure 5:
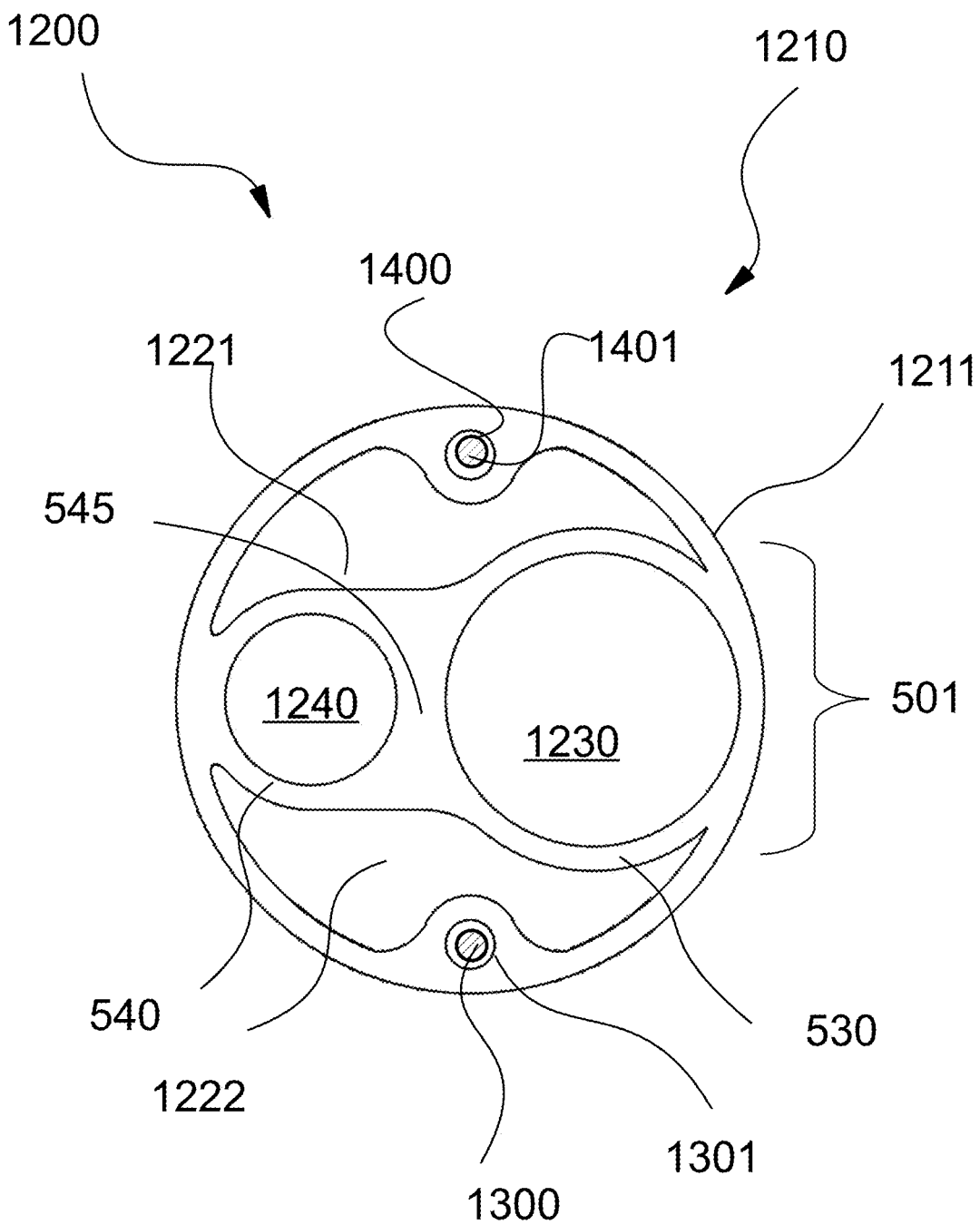
FIG. 5 is a transverse cross section view of the tip in FIG. 4.
Figure 6:
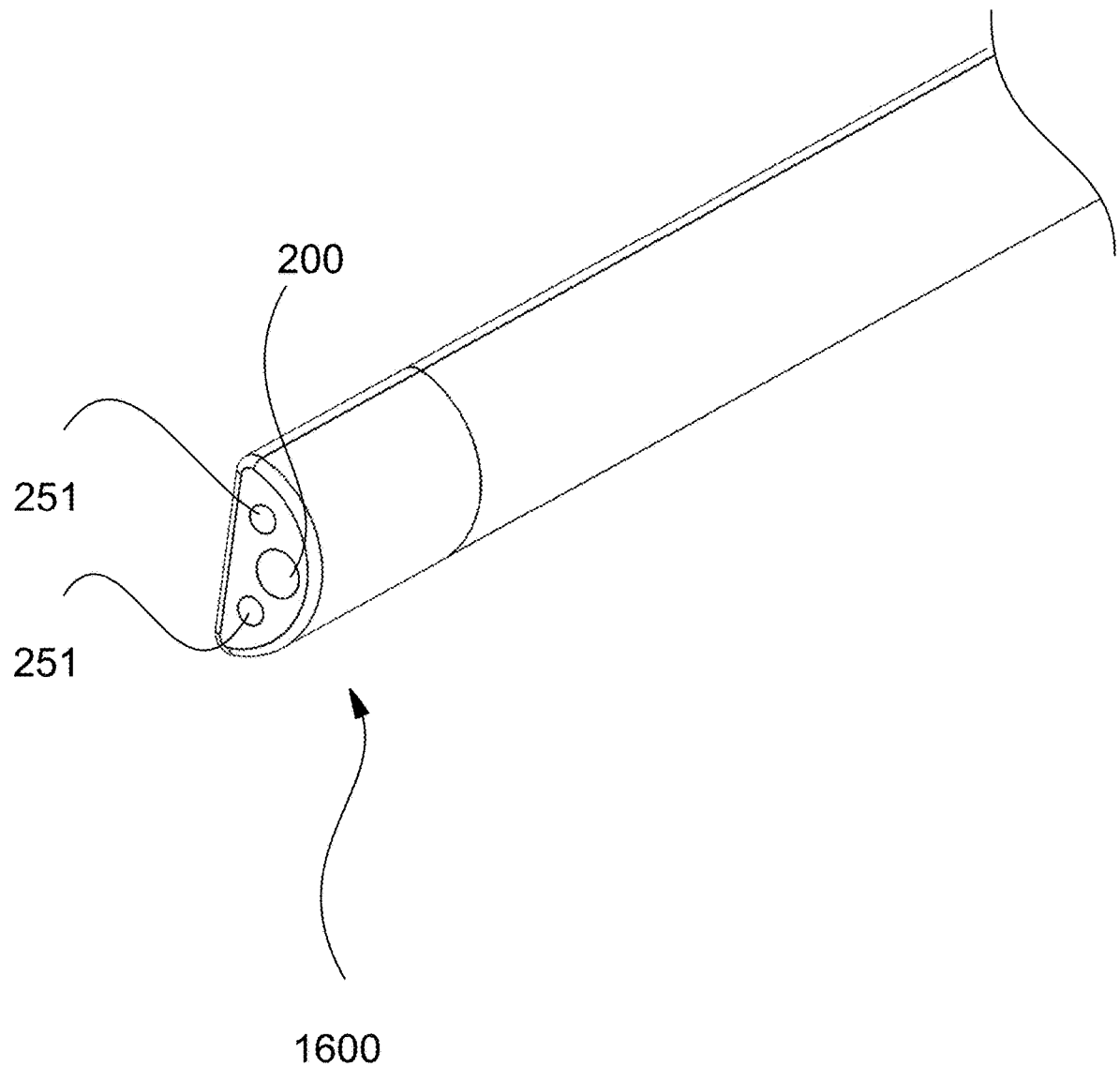
FIG. 6 is an isometric view of the tip of another embodiment with a "D" shaped control and imaging member for insertion in the disposable sheath shown in FIG. 7.
Figure 7:
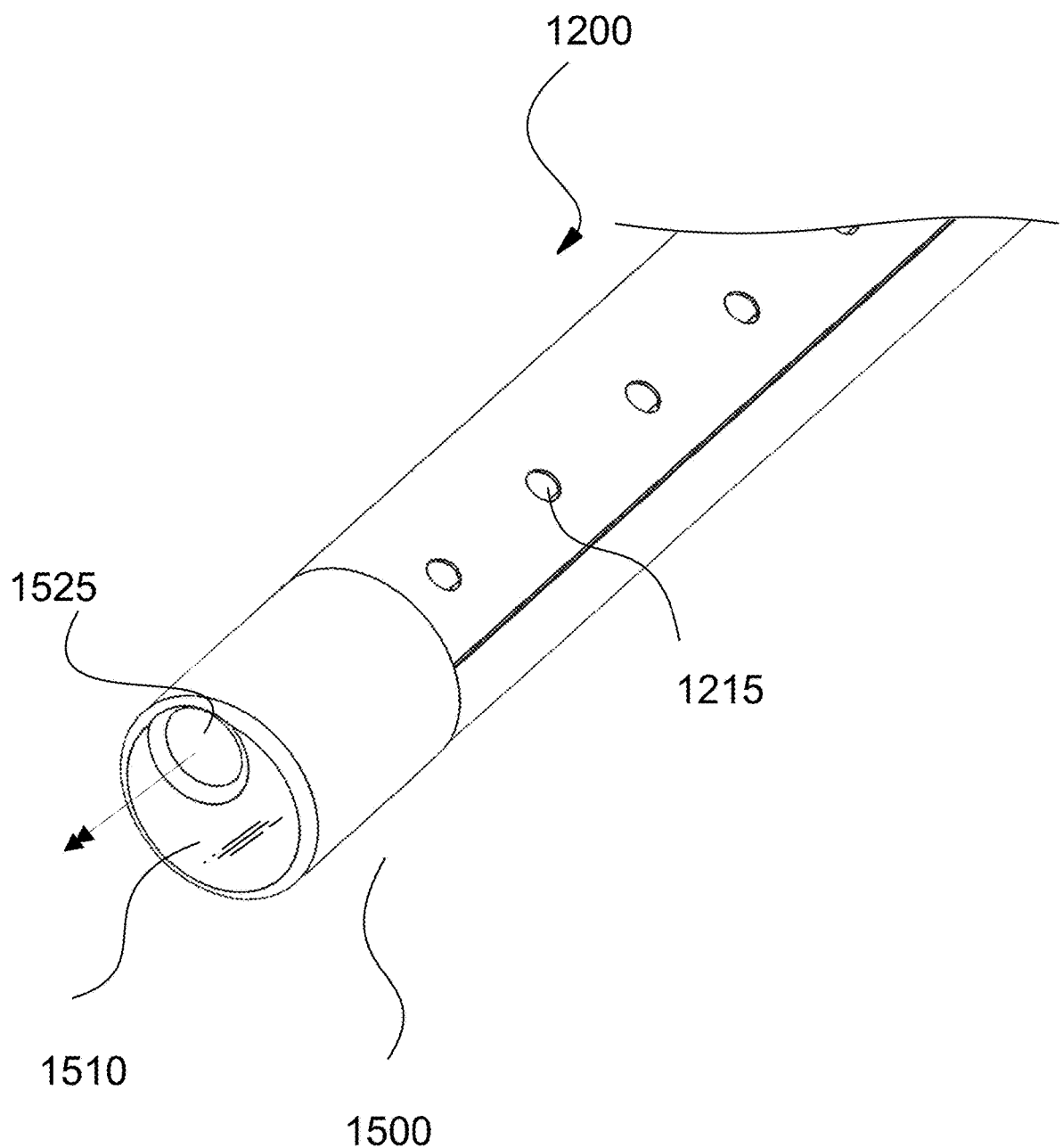
FIG. 7 is an isometric view of the tip of an embodiment of such a disposable sheath.
Figure 8:
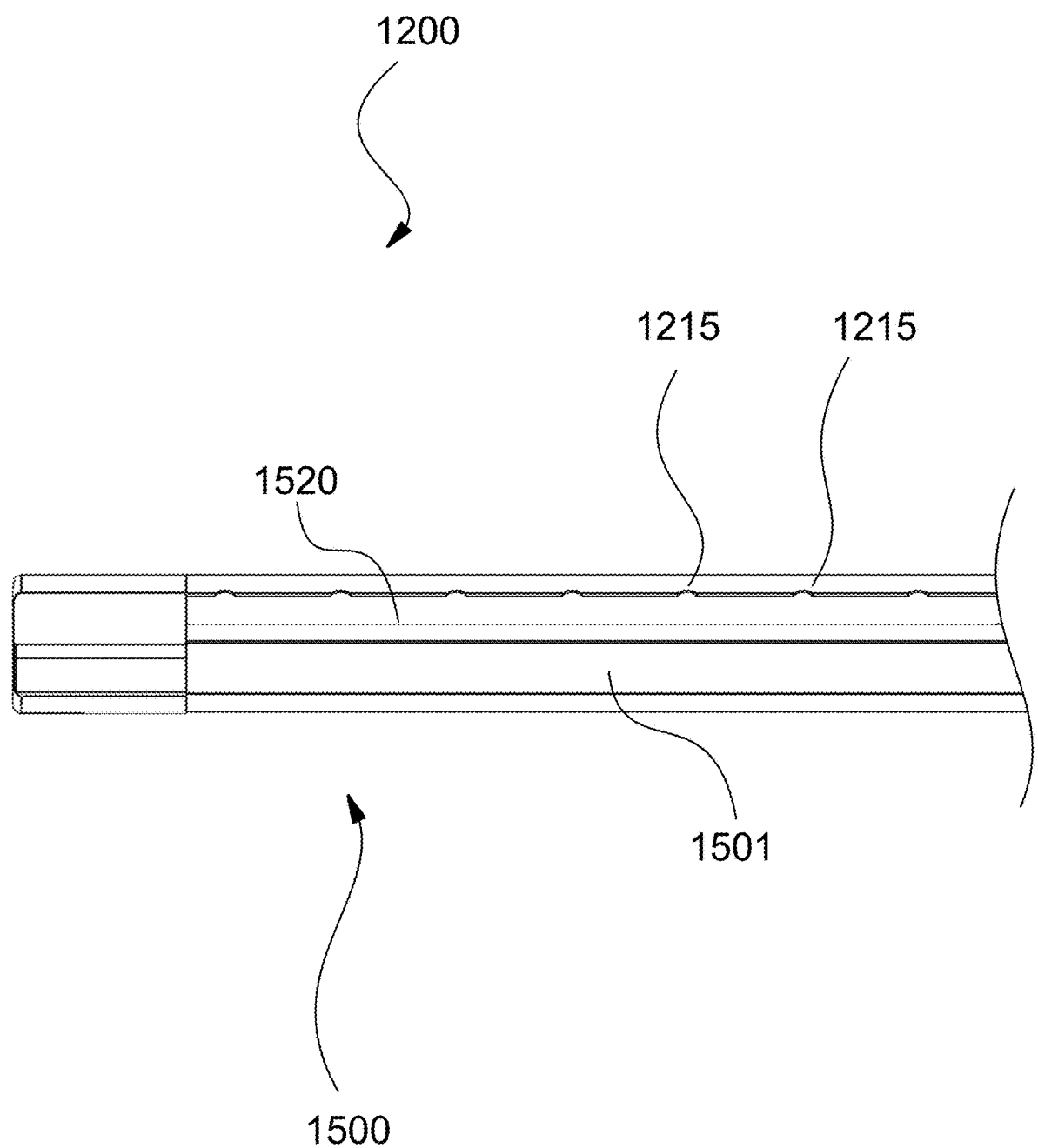
FIG. 8 is an axially disposed longitudinal cross sectional elevation view of the tip of an embodiment of such a disposable sheath.
Figure 9:
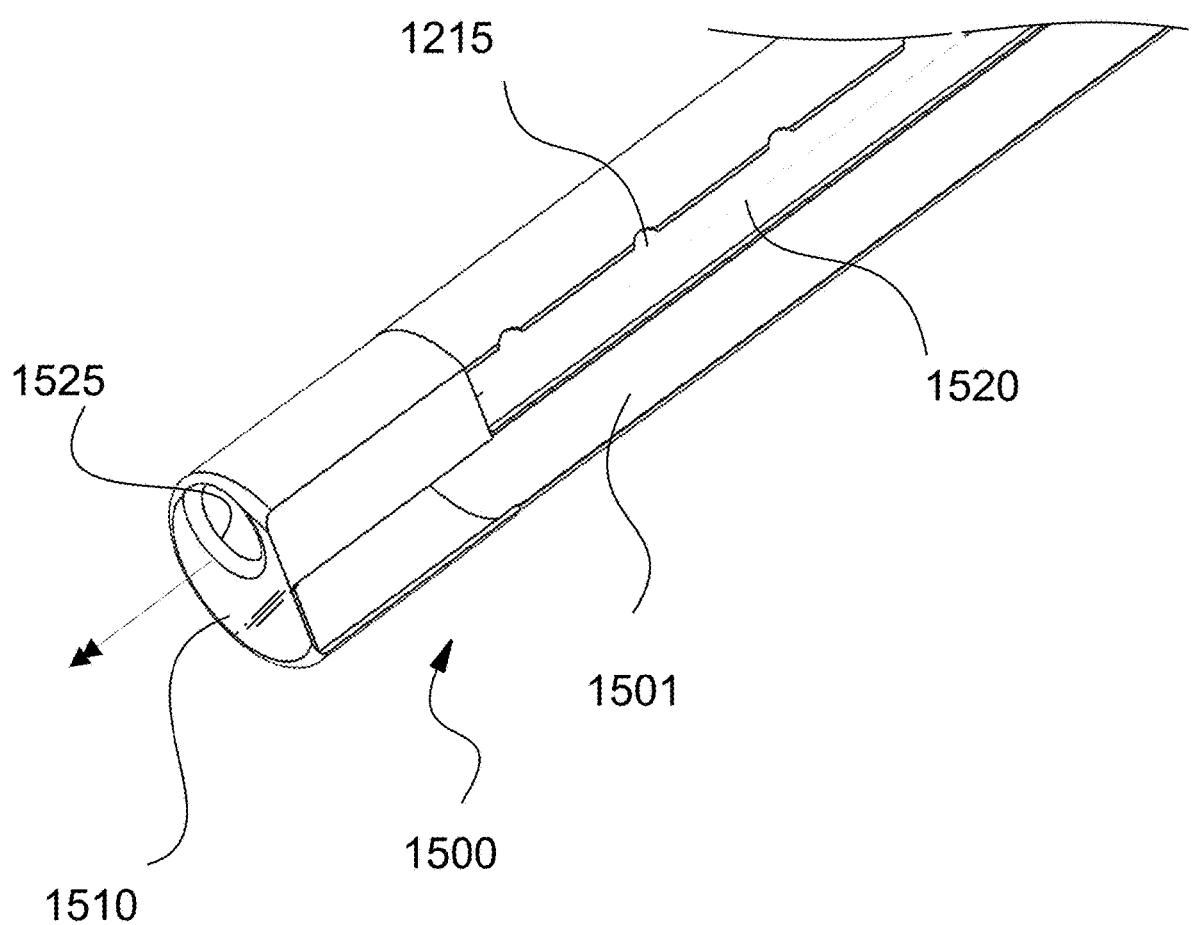
FIG. 9 is an offset axially disposed longitudinal cross sectional isometric view of the tip of an embodiment of such a disposable sheath.
Figure 10:
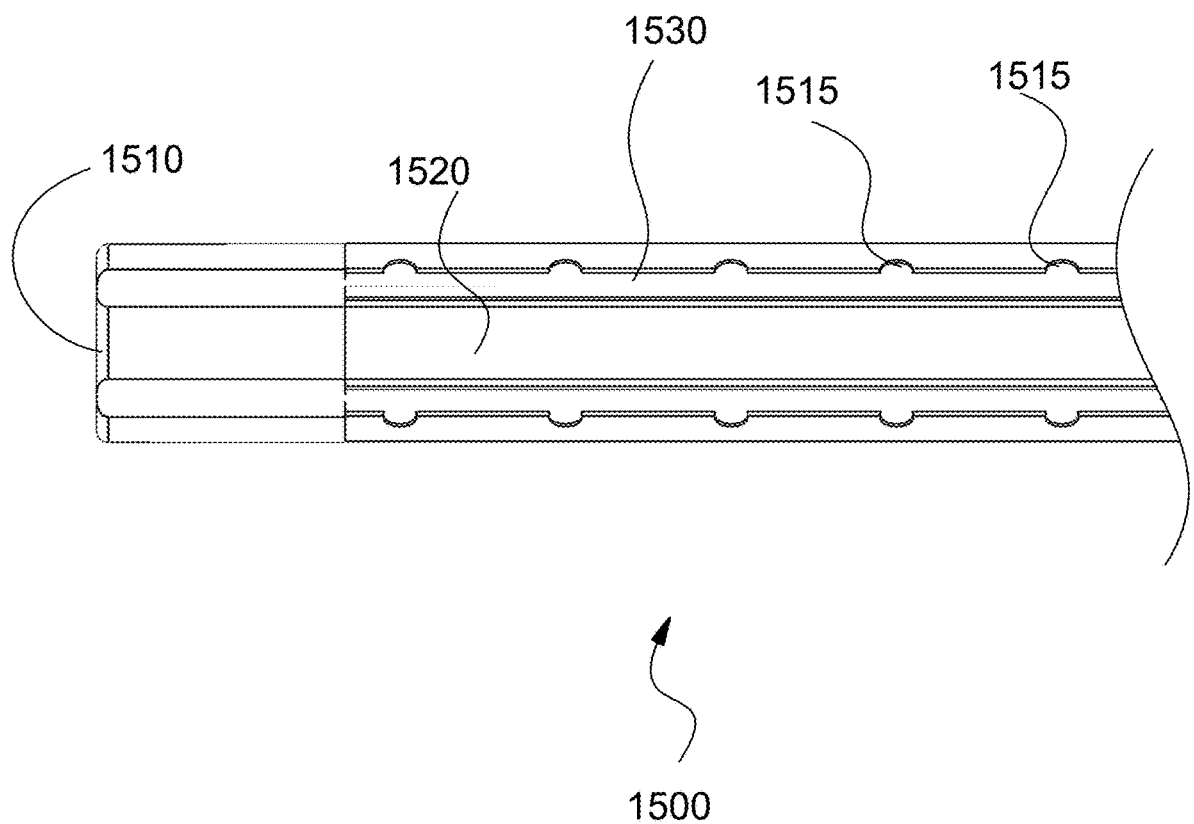
FIG. 10 is a different offset axially disposed longitudinal cross sectional elevation view of the tip of an embodiment of such a disposable sheath.
Figure 12:
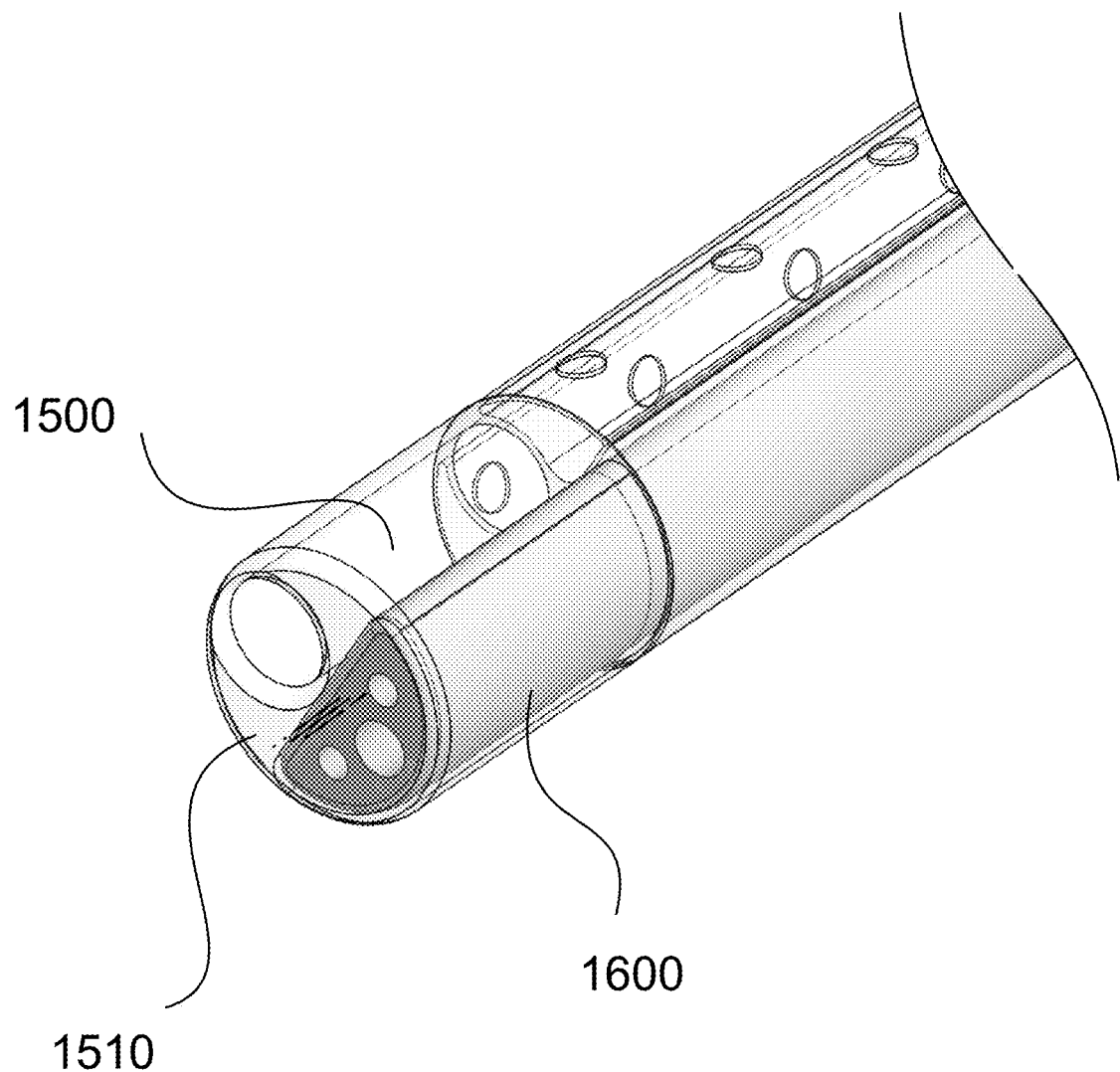
FIG. 12 is a cut away perspective view of the sheath including the inserted "D" shaped member illustrated with surface shading.

In the preferred embodiment illustrate in FIG. 5, a first 1221 and second lumens 1222 are disposed at least partially on opposing sides of the tube wall have perforations 1215 through the wall 1211. The couple catheter member 1200 preferably has a working length of at least about between 55 and 115 cm. The length of at least about 55 cm allows it to reach the esophagus of most patients, whereas the longer working length of at least about 115 cm also allows it to reach the cardia/duodenum.

Figure 4:
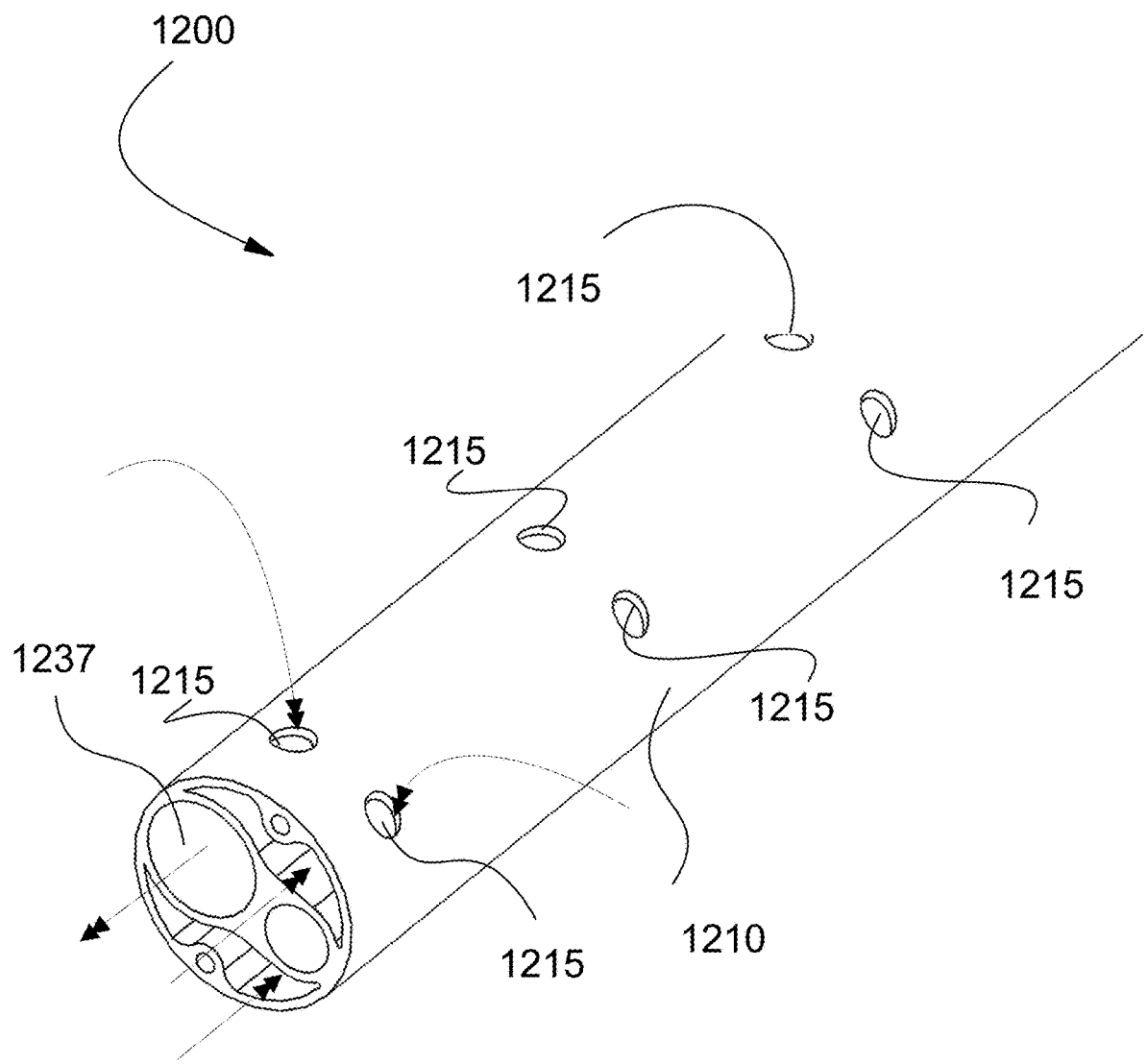
FIG. 4 is an isometric view for the tip or distal end of the catheter portion of the device in the FIG. 1-3 in a straightened or linear configuration.

Another aspect of the invention in various embodiment may include guide wires 1301 and 1401 in at least two of the lumens 1300 and 1400, which are disposed adjacent to the tube wall 1211 on opposite sides of the tube 1210, as illustrate in FIG. 4. For example, each of the first and second lumens partially surround the opposing pair of lumens having guide wires. The control actuator/hand-piece that receives the tubes may deploy conventional means to engage the guide wires.

The remaining lumens 1230 and 1240 are for imaging and fluid spray means and may be disposed between the first and second lumens. Lumen 1230 is open at portal 1237 to introduce a tool or material, whereas lumen 1240 is for imaging and generally contain fiber optic imaging lens or camera 200 and Light Emitting Diodes (LED) 251 and 252 or optical fibers used to transmit light from LED's in the controller 100.

It should be noted that the remaining lumens 1230 and 1240 are disposed adjacent to a central axis of the tube 1210 such that they are at least partially surround by the first and second lumens 1221 and 1222. A liquid freezing agent may be introduced directly via lumen 1230 or 1240 or another tube with a spray orifice guided into the lumen 1230, as illustrated and described further below. Such delivery of the liquid freezing agent may be by any fluid spray means optionally in another lumen at the distal end of the tube In any of the above and following embodiment the imaging means is a micro-camera or a fiber optic imaging device 200. The imaging means is a camera 200 that captures light outside of the visible spectrum, such as infrared light. Infrared imaging provides user with pathology differentiation for precise delivery of fluid freezing agent or other cryotherapeutic fluid, such as a cold liquid that becomes a gas on warming (for example liquid nitrogen), or a cold gas (such as carbon dioxide). Infrared imaging can provide user with visual indication of where cryotherapeutic liquid has already been delivered because the frozen tissue is colder, and remains cold until it is warmed by conduction, as it lacks vessel to warm by the convection from blood flow, as the blood capillaries are destroyed by freezing. Alternative imaging modalities to visible light (Optical Coherence Tomography, chromoendoscopy, etc) for indicating pathological tissue to target with cryogenic fluid.

FIG. 6-12 illustrate another embodiment of the invention in which a device 1000 has a disposable protective portion 1500 that cover the permanent portion 1600, avoiding the need to sterilize the device disposable lumen with a sealed protective sheath for a re-usable catheter with the imaging and illumination means.

Figure 21:
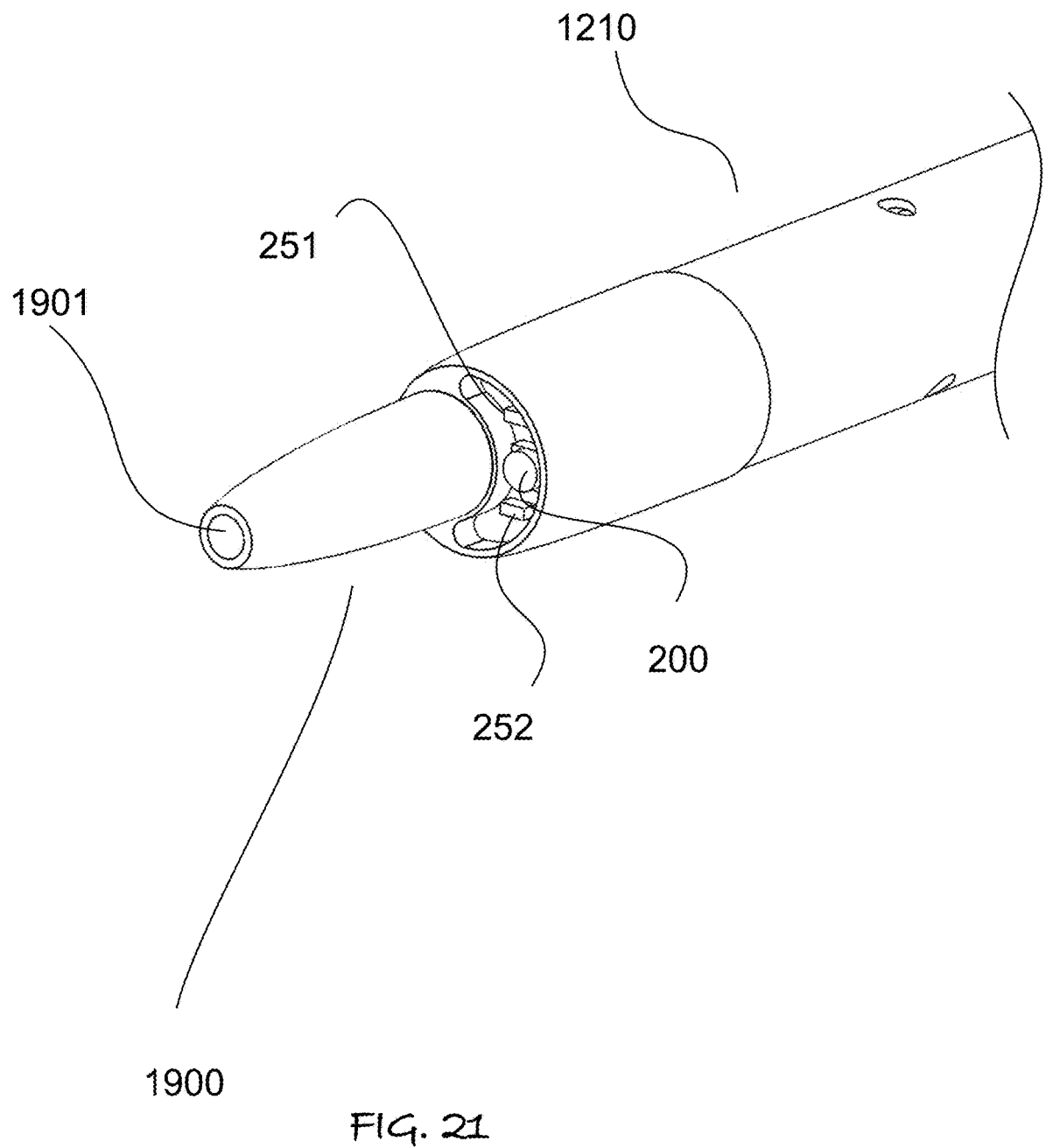
FIG. 21 is an isometric view of another embodiment of the invention showing an applicator tip advanced beyond the imaging means at the distal end of the tube.
Figure 22:
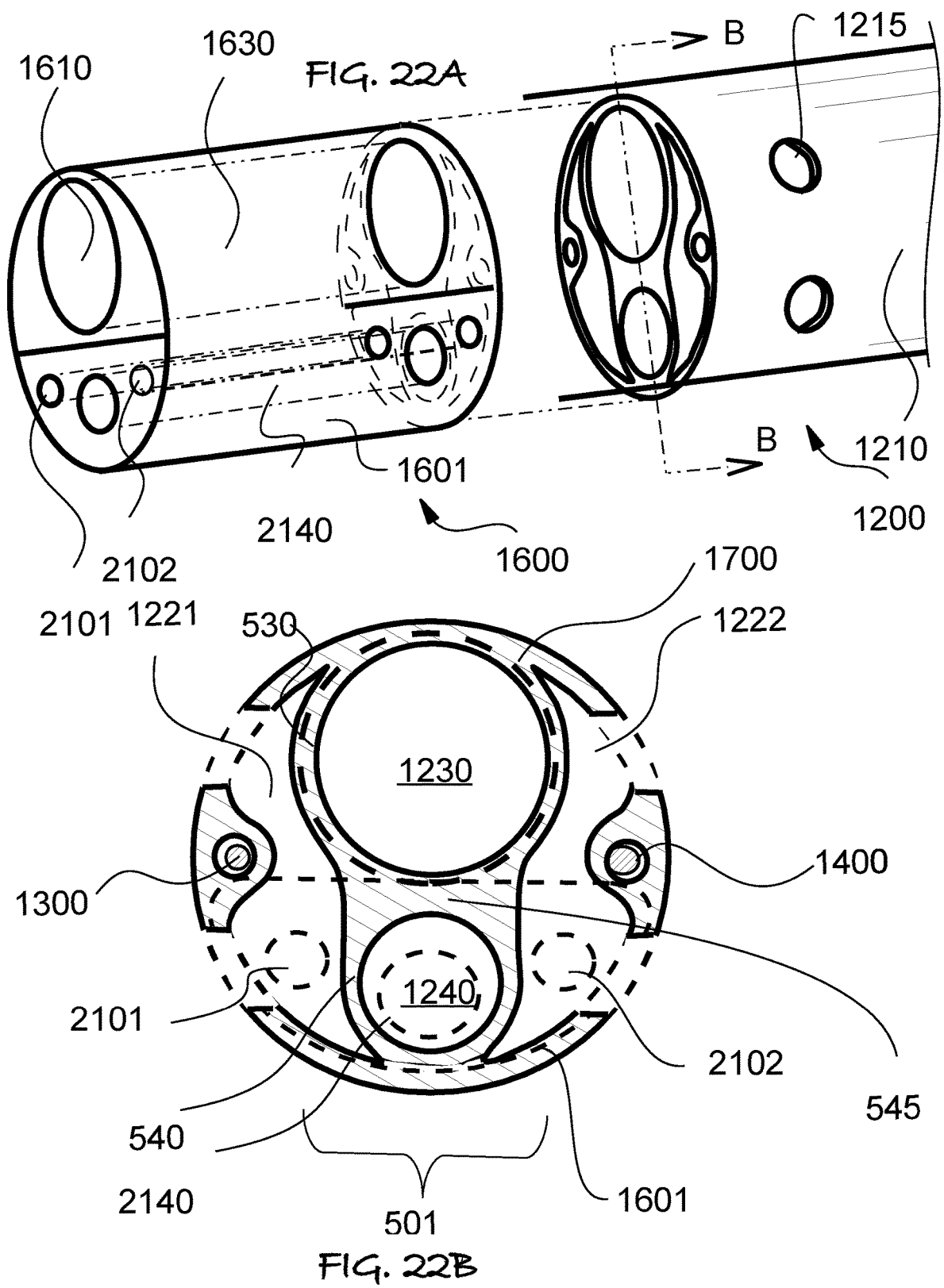

As the lumen for the permanent member 1600 is sealed at the distal end and side, it keeps the permanent member 1600 isolated from the body to avoid the need for sterilization The permanent portion 1600 is an elongated endoscopic catheter tube 1210 with a "D" shape that has imaging and illumination means. The disposable protective portion 1500 is a subdivided tubular sheath with a D shaped lumen 1501 to receive the permanent portion 1600 with a clear window 1510 on the end of the tube. The sheath 1500 has a lumen 1520 with a distal opening 1525. Lumen 1520 may also have side openings 1215. Alternatively, as shown in FIG. 10 and FIG. 11A-C, tube 1210 may include another lumen 1530 with side opening 1215 that runs parallel to the lumen 1220 with the distal opening. In this case lumen 1520 can be sealed at the side wall 1211 of the tube 1210 or by surrounding walls of lumen 1530. A treatment agent or tool can be introduced via lumen 1520. For example, the elongated tube 1900 with an end opening 1901 such as shown in FIG. 21 may be introduced into lumen 1520. Lumen 1520 that is used to deliver a cryo-fluid may also have a heater coil 1700, as is further discussed with respect to FIG. 13A-C and FIG. 14.

It should be appreciated the disposable portion 1500 may be constructed by adhering or fusing the distal end of tubular member 1512 to a tip portion 1511, each of which is illustrated in transverse sectional views in FIGS. 11C and 11B respectively. The tip 1511 with the window 1510 can be fabricate by casting resin or another form of molding, including 3-D printing, around a rigid glass or plastic window, 1510, and member 1512 (or 1210) can be made by co-extruding plastic resin to form the outer diameter of the tube and the connected interior lumens. Alternatively, tube 1512 or 1210 can be made by laminating tubes of other extruded profile that are closed to form lumens to an elongated flexible plastic member. The plastic member can be rolled transversely to connect to the opposite edge or another lumen to form the tube, with an edge seam formed by ultrasonic welding or adhering with adhesive resin. The initial lamination before rolling into a tube can be forms by adhesively laminating multiple tubes to one of each other and the elongated plastic member, or co-extruding the elongated plastic member around the preformed tubing. The preformed tubing can be chemically or radiation cross linked after extrusion to avoid melting during co-extrusion. Mechanical control and power or signal transmitting wires, or optical fiber wires can also be co-extruded around or inserted after forming, or before any step of forming the tubular lumen 1210, such as by rolling or a final extrusion step. Perforation 1215 can readily be formed by laser ablation at any stage in fabrication, whereas punching out of perforations with mating dies is preferably performed with a plastic member before it is rolled into a tube.

Figure 13A:
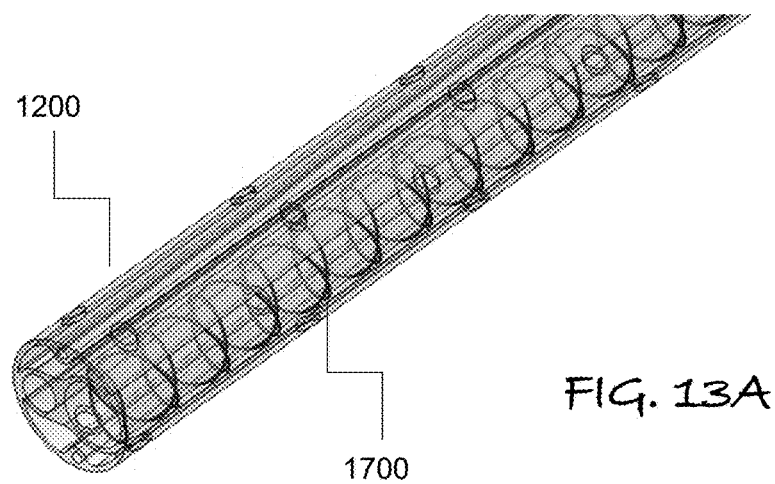
Figure 13B:
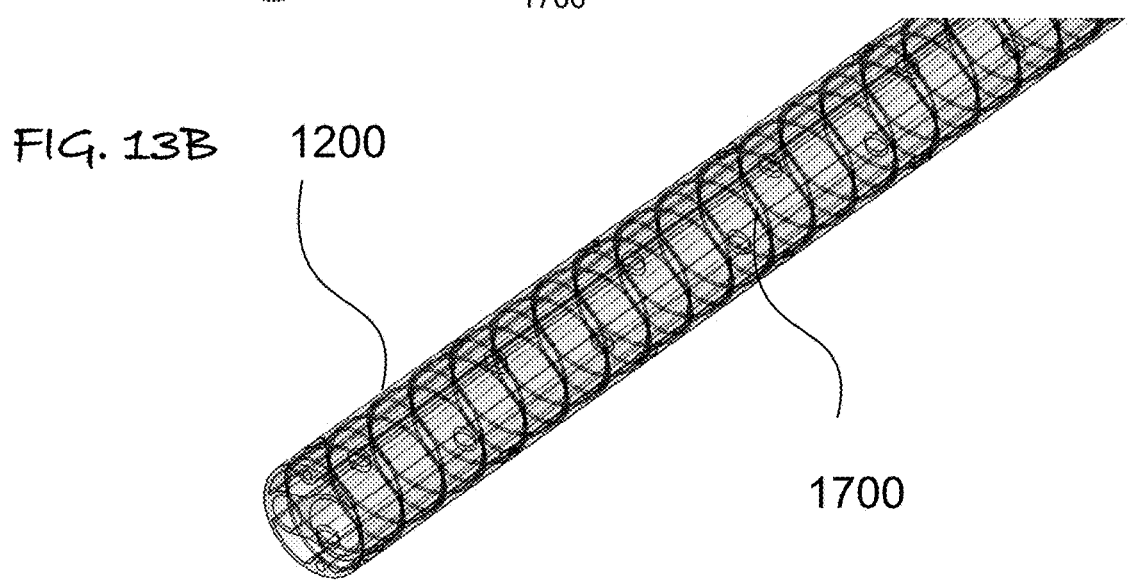
FIG. 13B illustrates an alternative position for the heating element and FIG. 13C illustrates another embodiment in which the heating element is deployed in the sheaf type tube of FIG. 12.
Figure 13C:
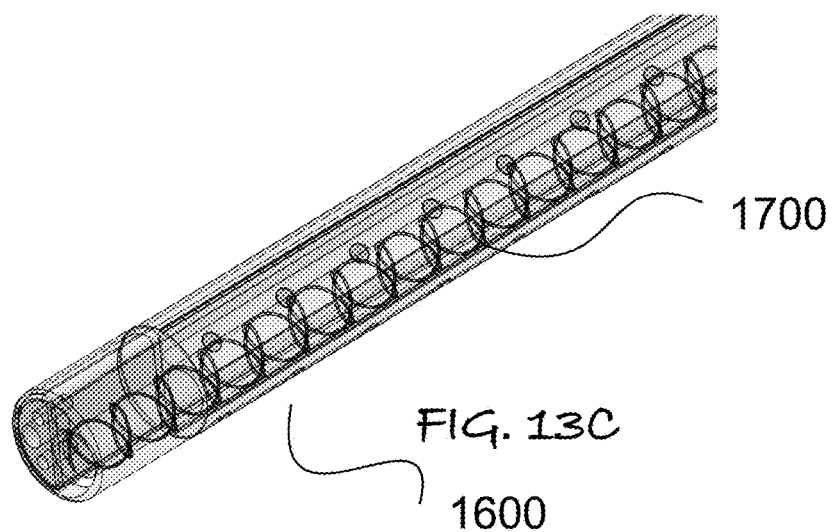

FIG. 13A-C and FIG. 14 illustrate other preferred embodiments of the catheter for use with any of the embodiment of the device 1000, may include a heater means 1700 to prevent the clogging of the lumen from frozen bodily fluid or treating agent, or fluid or saline solution that might be used to clear the operating field. The heating means is preferably resistance heater coils 1701 connected by a circuit to a power source at the controller 100. Alternative locations for placing the heater coils is in the outer wall of the tube, or in the cryo-fluid delivery lumen 1230. FIG. 13A-C illustrate such embodiments in which the heater 1701 can be in any lumen used for cryo or liquid treating agent. Alternative placements of the wire 1710 that form the circuit between a power supply and the control 100 with the heater elements 1701, such as coils, may be inside a lumen, fused to the interior of lumen wall, or within the walls that define the lumen opening. Such heating wire can be externally wrapped or wound around the tube 1210, and then overcoat with a thin layer of resin or varnish to become a part of the device 1210. Electrical connections to extruded wire in the tube 2010 can be made before such overcoating.

FIG. 15-20 illustrate embodiments of a fixation and/or dilation means 1800 near the distal end of the tube. The fixation means may be an expandable tubular body 1810 that surrounds the exterior of the tube 1210, and includes a means to selectively pressurize and deflate the inflation fixation means, such as a tube 1820 in fluid communication with a source of pressure at the controller 100. Placement of the inflation fixation means or tube 1810 from the distal end of the tube is at least about 10 mm (more preferably at least 20 mm, and most preferably at least 30 mm). Pressurization can be with gas (air or nitrogen for example) or a fluid (water for example). Such a fixation means may be an expandable tubular member or body 1810 in fluid communication with another lumen 1820 that extends toward the proximal end of the tube or an external cannula 1830 (FIG. 19) that is fused to the outer wall of the tube to extend from about the proximal end to form a fluid connection with the inflation fixation means. Lumens 1820 or 1830 may extend along or in the tube 1210 to the controller 100, but will have a lateral opening 1825 into the expandable tubular member 1810.

Figure 16A:
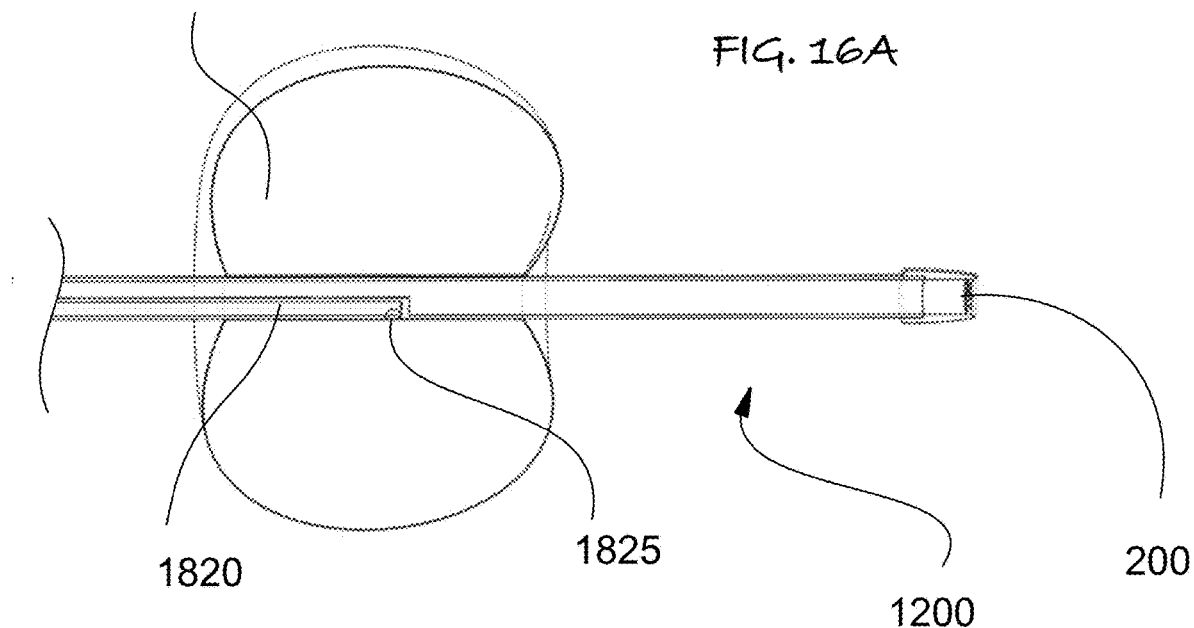
Figure 16B:
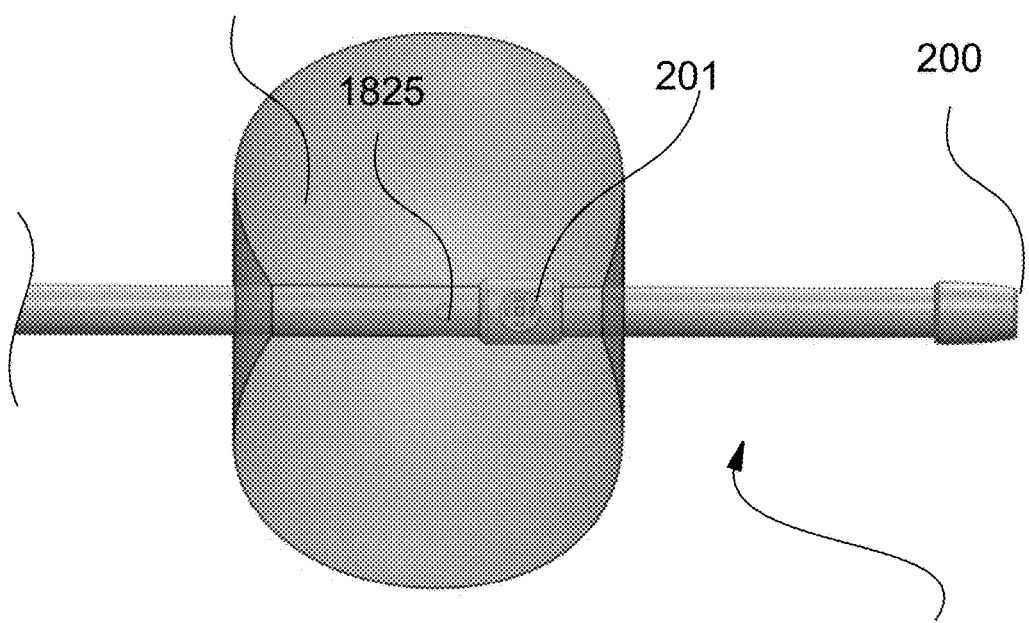
FIG. 16B is a similar section view of the inflated balloon in another embodiment in which an imaging means is disposed in the balloon.

The expanded tubular member 1810 may have a convoluted wall or surface when not expanded, as shown in FIG. 16A, but can form a smooth uniform curvilinear surface when expanded as shown in FIG. 16B. The expanded tubular member 1810 member may be configured to form any shape when inflated via lumen 1820 or 1830.

As some treatment modalities may results in strictures when new tissue on walls of the healing esophagus has a tendency to adhere narrowing or partially closing the esophageal passage, another aspect of the invention is a device and method of the opening such strictures mechanically by the inflation and fixation means, either as a separate treatment, or as a preliminary step in any of the aforementioned or future treatment processes.

In addition to the method of introducing a liquid freezing agent for treatment after introducing the tube 1210, imagining the area to be treated, and fixing the tube 120 if necessary, the treatment method can include stricture opening with the inflatable fixation means prior to starting any treatment or alone as a treatment. Such treatments, with or without the need for treating strictures may include alternative treatment modalities to cryogenics include RF ablation, photodynamic therapy. It should also be appreciated that such treatments may include application of negative pressure to aide in evacuation of fluids from within the patient via any lumen open at the distal end of tube 1210.

It should now be appreciated that aspects of the invention include methods of using an endoscopy tube or a covered endoscopy tube that is inserted into a body cavity of a patient from the nasal cavity of the patient and the body cavity is the esophagus.

Another aspect of the invention is a method of using an endoscopy tube or a covered endoscopy tube that is inserted into a body cavity of a patient from the mouth of the patient and the body cavity is at least one lung.

Figure 17A:
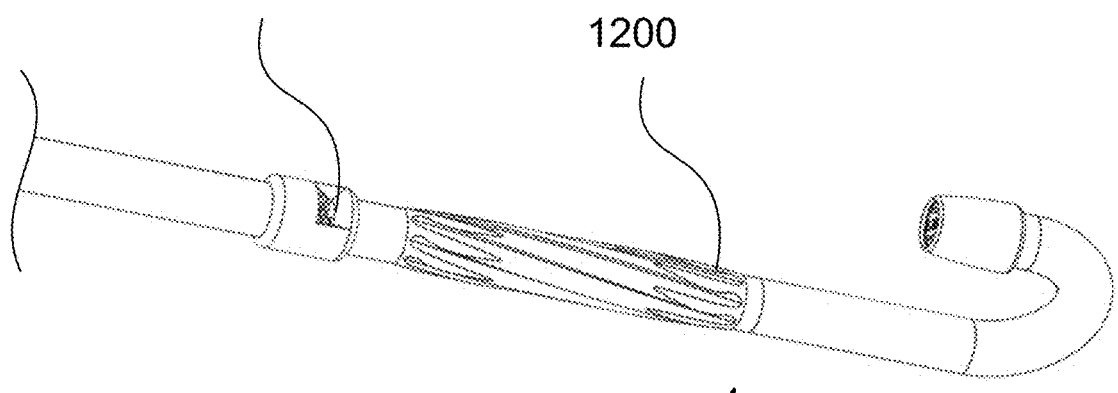
Figure 17B:
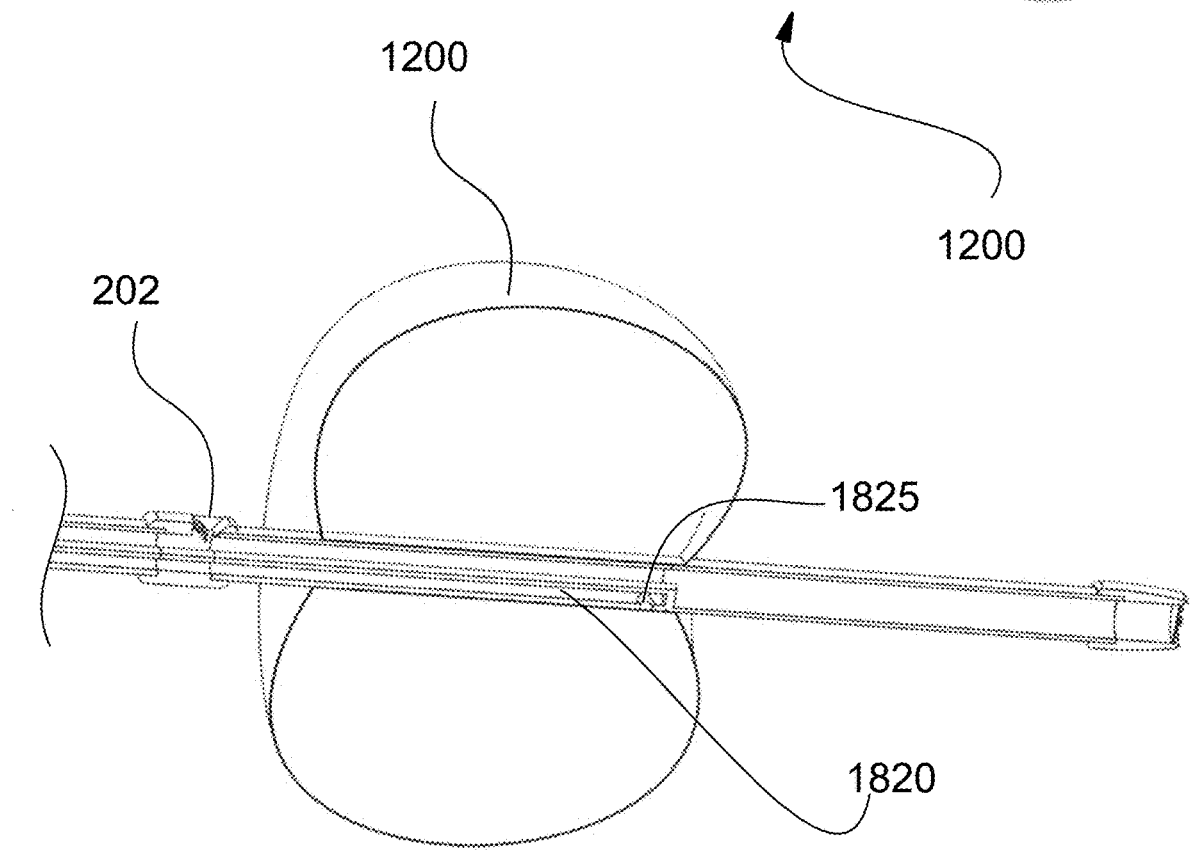
FIG. 17B is a longitudinal sectional isometric view thereof with the balloon inflated.
Figure 18:
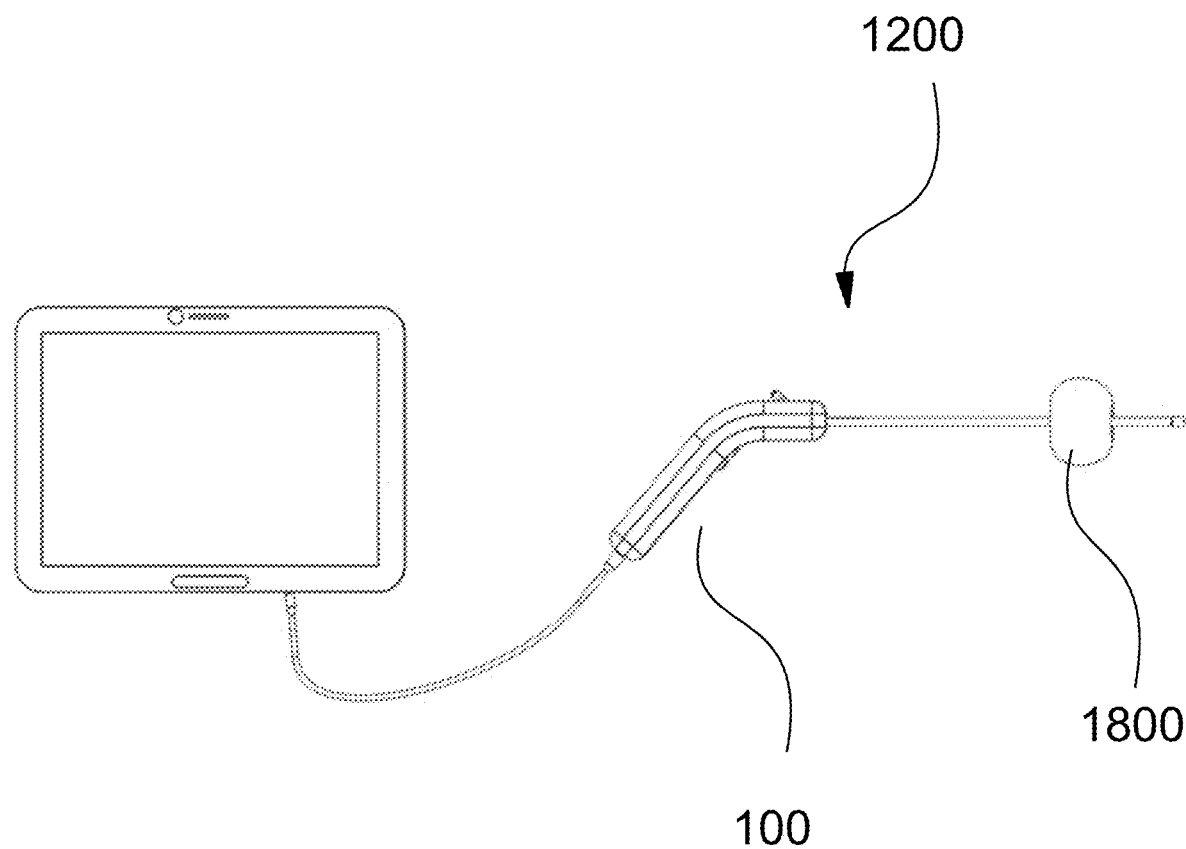
FIG. 18 is a schematic diagram of the device in signal communication with a portable display monitor.
Figure 19:
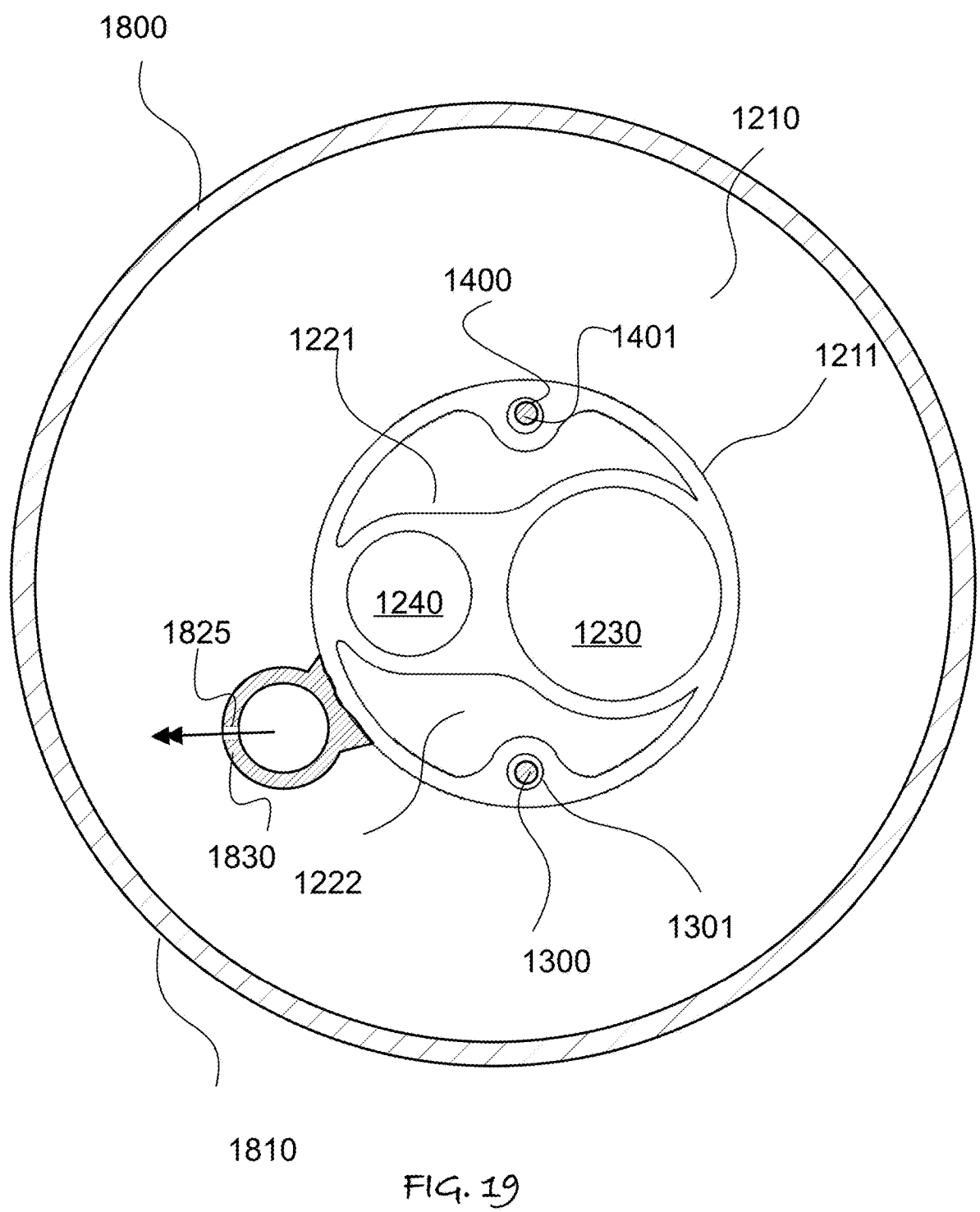
FIG. 19 is a transverse cross-section view of the balloon inflator surrounding the tube of another embodiment related to FIGS. 4 and 5.
Figure 20:
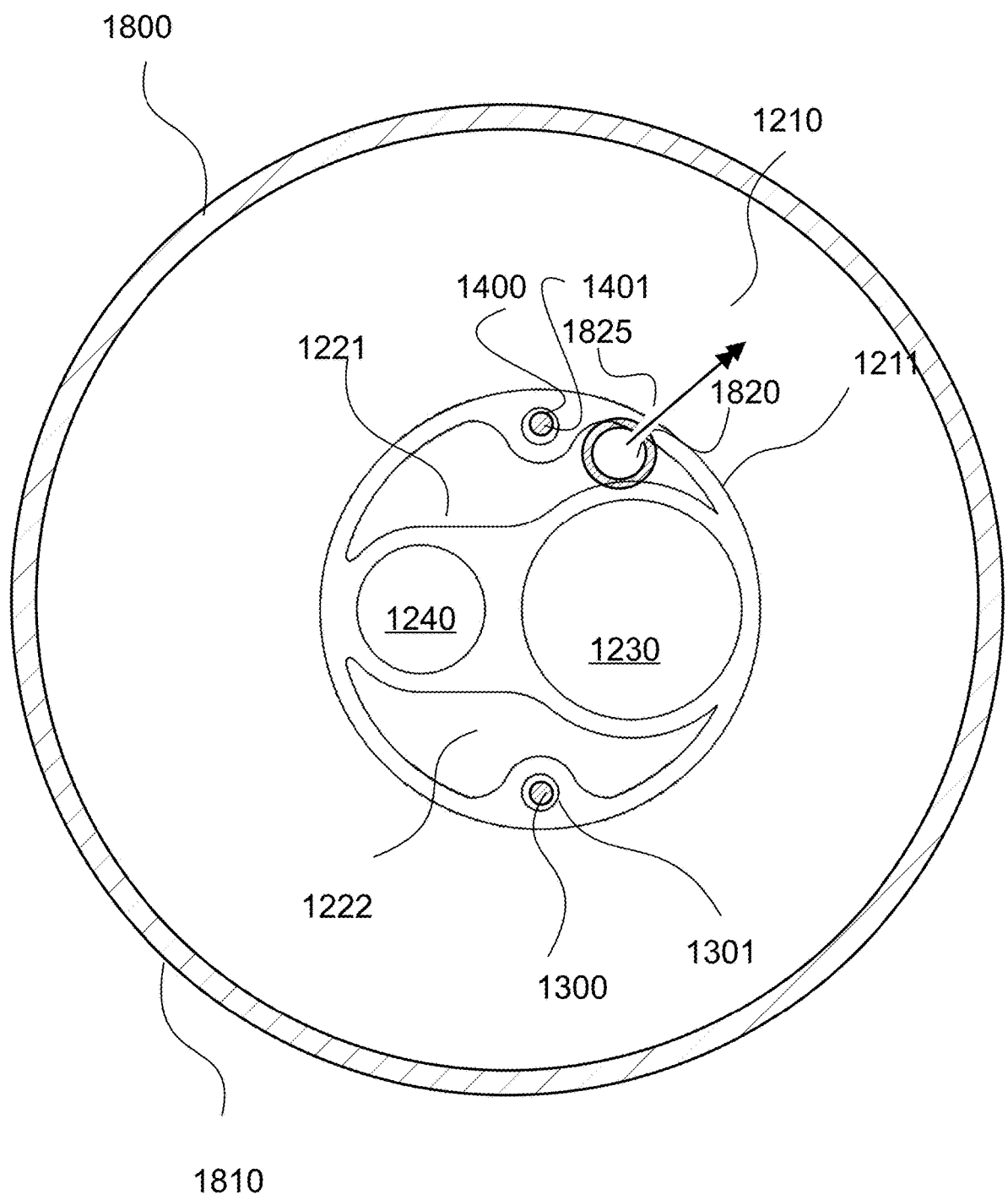
FIG. 20 is an alternative embodiment of the inflator surrounding the tube in FIG. 19.

As such treatment may require the ability to locate the structure to optimally place the balloon member 1800 before expansion, FIG. 16B-FIG. 17B illustrate alternative locations for placing a second camera such as 201 in the balloon 1800, or above the balloon for camera 202 as shown in FIGS. 17A and 17B. Accordingly, the device illustrate in FIG. 15A to 18 can be used for locating the area that requires dilation with any of cameras 200, 201 and 202, inflating the balloon 1200 to open a stricture and withdrawal of the device, either a stand alone treatment, or as a step prior to subsequent treatment of the underlying condition at or proximal to the point of stricture that was opened.

FIG. 21 illustrates another embodiment of the invention that provides placement of treatment modality tool 1901 beyond the camera 200 to image the progress of treatment. A fluid spray means (or a tool for any alternative treatment modality, such as without limitation, electrodes or photo therapy illumination means), such as a nozzle 1901 can be inserted via lumen 1230 beyond the distal end of the tube 1210 so the region of the spray application of the liquid freezing agent, is accessible to the imaging means, such as camera 200.

Alternatively, the lumen 1230 that is used to introduce a liquid freezing agent or other treatment modality can be fixed to extend past the lumen 1230 with the imaging means, such as camera 200 and Light Emitting Diodes 251 and 252.

FIG. 22A and FIG. 22B are intended to illustrate, in an isometric view of another embodiment of the invention, that the applicator tip 1901 of FIG. 21 can be advanced beyond the imaging means at the distal end of the tube 1200 from a portion 1601 through a lumen 1630 open at end 1610 so that fluid enters via lumen 1230. FIG. 22B shows the alignment of lumens 1230 and 1630. In the embodiment of the invention of FIGS. 24A and 24B, the device 1000 has disposable protective portion 1500 that covers the permanent portion 1600, avoiding the need to sterilize the device disposable lumen with a sealed protective sheath for a re-usable catheter with the imaging and illumination means. As a lumen 1501 for the permanent member 1600 is sealed at the distal end and side, it keeps the permanent member 1600 isolated from the body to avoid the need for sterilization. The permanent portion 1600 is an elongated endoscopic catheter tube with a "D" shape that has imaging and illumination means. The disposable protective portion 1500 is a subdivided tubular sheath with a D shaped lumen 1501 to receive the permanent portion 1600 with a clear window 1510 at the distal end. The sheath 1500 has lumens 1520 and 1530 that extends parallel to the D shaped lumen 1501. Lumen 1520 is for the fluid spray means and extends though lumen 1530 to the distal opening 1525. The sealed lumen 1501 is for the imaging means and contains the guide wires 1301 and 1401 that are coupled to the imaging means and is terminated in a sealed window 1510 for protecting the imaging means, which includes camera 200 and LED's 251 and 252. Lumen 1530 has the perforations 1525 in the outer wall of the disposable protective portion or sheath 1500. 501 is a cross section of the tube, 530 is a portion of the ovoid shape that creates lumen 1230, 540 is a portion of the ovoid shape that creates lumen 1240, and 545 is webbing that connects the portions of the ovoid 530 and 540, 2101 is a first lumen in the distal rigid portion that accepts a light emitting element, and 2102 is a second lumen in the distal rigid portion that accepts a light emitting element, 2140 is a third lumen in the distal rigid portion that accepts an imaging element.

The permanent portion 1600 is an elongated endoscopic catheter tube with a "D" shape that has imaging and illumination means. The disposable protective portion 1500 is a subdivided tubular sheath with a D shaped lumen 1501 to receive the permanent portion 1600 with a clear window 1510 at the distal end. The sheath 1500 has lumens 1520 and 1530 that extends parallel to the D shaped lumen 150. that has a distal opening 1525. Lumen 1520 is for the fluid spray means and extends though lumen 1530 to the distal opening 1525. The sealed lumen 1501 for the imaging means and contains the guide wires 1301 and 1302 that are coupled to the imaging means and terminated in a sealed window 1510 for protecting the imaging means, which includes camera 20 and LED's 251 and 252. Lumen 1530 has the perforations 1525 in the outer wall of the s disposable protective portion or sheath 1500.

Figure 23:
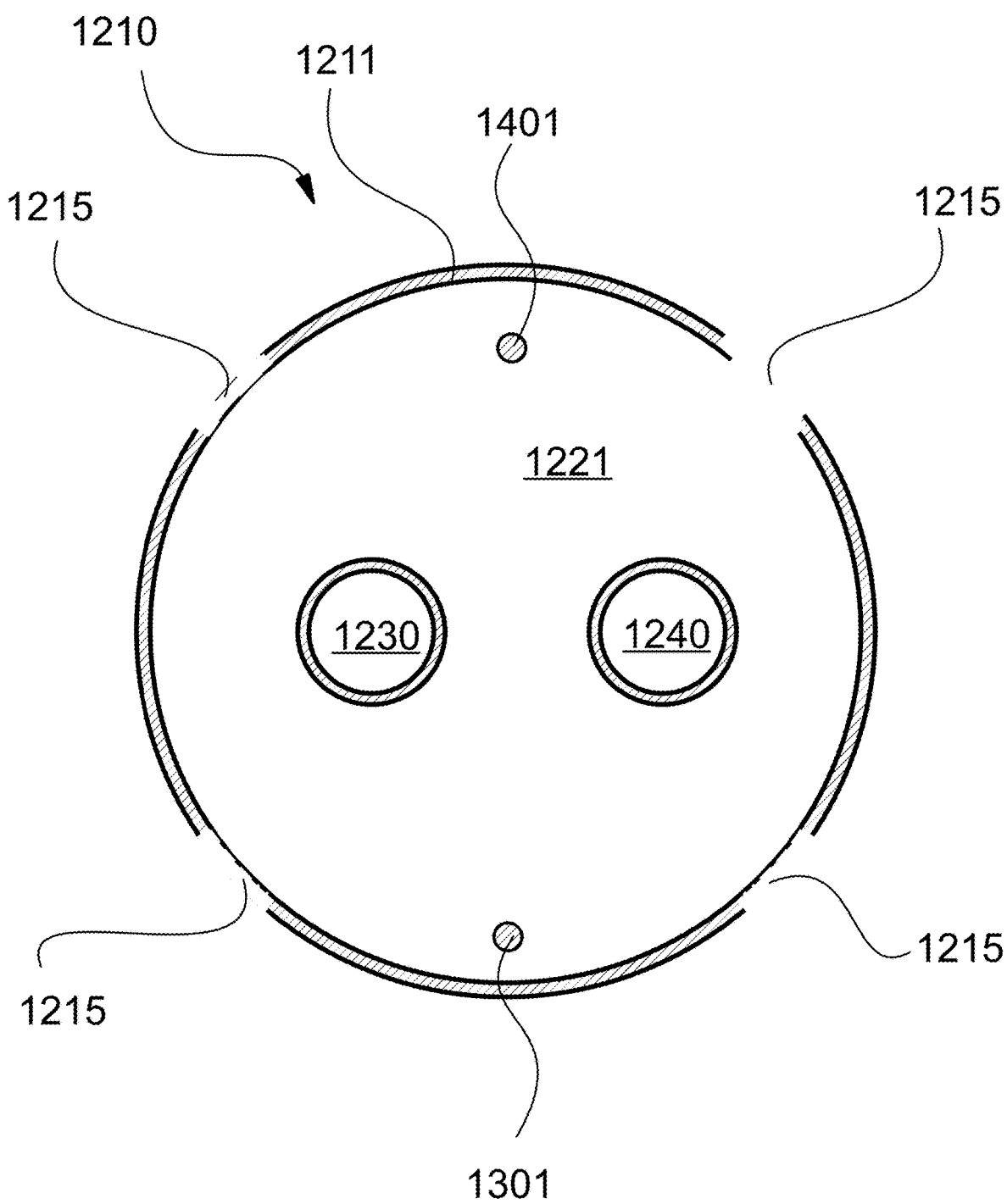
FIG. 23 is a transverse cross-sectional view of another embodiment of the tube.

FIG. 23 illustrates another embodiment of the tube 1210 in section view with two guide wires 1301 and 1401 roughly opposed within a first lumen 1221. This first lumen is defined by the outer wall 1211 of the tube 1210. The two guide wires 1301 and 1401 allow articulation by tension at the controller 100. Lumens 1230 and 1240 are for imaging means and fluid spray means, such as cryogen delivery, respectively and also may be disposed within a first lumen 1221. Lumen 1230 may contain or be replaced by electrical and/or fiber optical cable for the imaging system. The outer wall 1211 will have a plurality of perforation 1215 that penetrate to the first lumen 1221 generally around the distal portion to accept the expanding gasses from the evaporating cryogen after delivery to the outside of the tube 1200 via an exit orifice of lumen 1240. These tubes that form lumens 1230 and 1240 or cables and lumen 1240 are fixed in place adjacent opposing end of the tube 1210, as are guide wires 1301 and 1401, and can move within the inner space of the catheter between the two ends. This inner free space with the interior of the should generally be greater than about 6 mm² to work clinically and evacuate the expanding gas that formed on the warming of the liquid freezing agent introduced by the fluid spray means. By inner free space we mean the area within the interior side of the outer wall, minus the area of the guide wires and smaller interior lumens. However, if the total area within the outer diameter of the tube is over about 120 mm² would be too large to fit into the mouth or nose of most patients.

Although the various and preferred aspects of the various embodiments have been discussed with respect to use as an endoscope, nothing precludes their use as a laparoscope, a portion of a laparoscope or in a laparoscopic procedure.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

We claim:

1. A method of treating a patient comprising the steps of:
   a) providing a flexible tube having:
      i) a proximal end and an opposing distal end with an outer wall extending between the ends,
      ii) multiple parallel lumens that extend generally between the proximal and distal ends of the flexible tube, including at least a first lumen adjacent the outer wall of the flexible tube,
      iii) a plurality of perforations in the outer wall of the flexible tube that penetrate to a first lumen, wherein the first lumen has an upper vent portal adjacent the proximal end,
   b) providing a patient,
   c) introducing the distal end of the flexible tube through the nose of the patient into a nasal cavity,
   d) advancing the flexible tube from the nasal cavity into the esophagus,
   e) identifying an area of the esophagus to be treated,
   f) fixing the flexible tube such that the distal end of the tube is disposed adjacent to the area to be treated,
   g) introducing a liquid freezing agent into the proximal end of the tube for delivery via at least one of the multiple parallel lumens to exit a fluid spray means at the distal end of the tube,
   h) whereas a gaseous form of the liquid freezing agent expands on warming can flow toward the proximal end of the tube by entering the first lumen via the plurality of perforations therein, and
   further comprising the steps of preparing the flexible tube by;
      a. providing an endoscopy tube having,
         i) a steering means,
         ii) an imaging means disposed at the distal end of the endoscopy tube, and
         iii) an illumination means disposed at the distal end of the endoscopy tube,
      b. in which at least one of the multiple lumens in the flexible tube is an imaging lumen open at the proximal end and closed at the distal end by an optically transparent window,
      c. inserting the distal end of the endoscopy tube in the open proximal end of the lumen having the optically transparent window,
      d. advancing the distal end of the endoscopy tube within the imaging lumen toward the distal end of the flexible tube to dispose the imaging and illumination means adjacent to the optically transparent window for illuminating and obtaining images of tissues exterior to the flexible tube and when the flexible tube covers the endoscopy tube, wherein said step of advancing provides a covered endoscopy tube, in which the covered endoscopy tube forms the flexible tube in said step of introducing the distal end thereof into through the nose of the patient into a nasal cavity.

2. A method of treating a patient comprising the steps of:
   a) providing a flexible tube having;
      i) a proximal end and an opposing distal end with an outer wall extending between the ends,
      ii) multiple parallel lumens that extend generally between the proximal and distal ends of the flexible tube, including at least a first lumen adjacent the outer wall of the flexible tube,
      iii) a plurality of perforations in the outer wall of the flexible tube that penetrate to a first lumen, wherein the first lumen has an upper vent portal adjacent the proximal end,
   b) providing a patient,
   c) introducing the distal end of the flexible tube through the nose of the patient into a nasal cavity,
   d) advancing the flexible tube from the nasal cavity into the esophagus,
   e) identifying an area of the esophagus to be treated,
   f) fixing the flexible tube such that the distal end of the tube is disposed adjacent to the area to be treated,
   g) introducing a liquid freezing agent into the proximal end of the tube for delivery via at least one of the multiple parallel lumens to exit a fluid spray means at the distal end of the tube,
   h) whereas a gaseous form of the liquid freezing agent expands on warming can flow toward the proximal end of the tube by entering the first lumen via the plurality of perforations therein, and
   wherein the at least one of the multiple parallel lumens that provides an exit for the fluid spray means at the distal end of the tube has a heating means.

3. A method of treating a patient comprising the steps of:
   a) providing a flexible tube having:
      i) a proximal end and an opposing distal end with an outer wall extending between the ends,
      ii) multiple parallel lumens that extend generally between the proximal and distal ends of the flexible tube, including at least a first lumen adjacent the outer wall of the flexible tube,
      iii) a plurality of perforations in the outer wall of the flexible tube that penetrate to a first lumen, wherein the first lumen has an upper vent portal adjacent the proximal end,
   b) providing a patient,
   c) introducing the distal end of the flexible tube through the nose of the patient into a nasal cavity,
   d) advancing the flexible tube from the nasal cavity into the esophagus,
   e) identifying an area of the esophagus to be treated,
   f) fixing the flexible tube such that the distal end of the tube is disposed adjacent to the area to be treated,
   f) introducing a liquid freezing agent into the proximal end of the tube for delivery via at least one of the multiple parallel lumens to exit a fluid spray means at the distal end of the tube,
   h) whereas a gaseous form of the liquid freezing agent expands on warming can flow toward the proximal end of the tube by entering the first lumen via the plurality of perforations therein, and
   wherein multiple parallel lumens include, a) a first central lumen with a bore of a first diameter that is disposed within an ovoid member, the ovoid member being connected at a top and bottom to the outer wall of the flexible tube,
b) a second central lumen with a bore of a second diameter that is smaller than the first diameter, the second lumen being disposed within the ovoid member and adjacent to a first central member,
iii) wherein the first lumen having a plurality of perforations through the outer wall adjacent the distal end of the tube comprises a pair of generally lobe shaped elongated lumens, each being disposed between opposing sides of the outer wall of the flexible tube and an adjacent side of the ovoid member, one of said pair being the first lumen having a plurality of perforations through the outer wall adjacent the distal end of the tube, and the other of the pair being an additional lumen having a plurality of perforations through the outer wall adjacent the distal end of the tube.

4. A method of treating a patient comprising the steps of:
a) providing a flexible tube having:
   i) a proximal end and an opposing distal end with an outer wall extending between the ends,
   ii) multiple parallel lumens that extend generally between the proximal and distal ends of the flexible tube, including at least a first lumen adjacent the outer wall of the flexible tube,
   iii) a plurality of perforations in the outer wall of the flexible tube that penetrate to a first lumen, wherein the first lumen has an upper vent portal adjacent the proximal end,
b) providing a patient,
c) introducing the distal end of the flexible tube through the nose of the patient into a nasal cavity,
d) advancing the flexible tube from the nasal cavity into the esophagus,
e) identifying an area of the esophagus to be treated,
f) fixing the flexible tube such that the distal end of the tube is disposed adjacent to the area to be treated,
g) introducing a liquid freezing agent into the proximal end of the tube for delivery via at least one of the multiple parallel lumens to exit a fluid spray means at the distal end of the tube,
h) whereas a gaseous form of the liquid freezing agent that expands on warming can flow toward the proximal end of the tube by entering the first lumen via the plurality of perforations therein, and
and wherein the flexible tube further comprises;
a. an imaging means disposed at the distal end of the flexible tube, and
b. an illumination means disposed at the distal end of the flexible tube,
c. in which the fluid spray means includes a nozzle that extends beyond the distal end of the flexible tube and the imaging means such that a region of spray application onto the area of the esophagus is visible to the imaging means.

5. A method of using an endoscopy tube comprising the steps of:
a) preparing an endoscopy device by;
   i) providing a tubular member comprising;
      (1) a tube having a proximal end and an opposing distal end with an outer wall extending between the ends,
      (2) multiple parallel lumens that extend generally between the proximal and distal ends of the tube, including at least a first lumen adjacent the outer wall of the tube,
      (3) a plurality of perforations in the outer wall of the tube that penetrate to the first lumen, wherein the first lumen has an upper vent portal adjacent the proximal end,
      (4) a second lumen that is open at a proximal end and closed at a distal end and having an optically transparent window at the distal end of the tube,
      (5) a third lumen open at the proximal end and the distal end for transporting a liquid freezing agent to a region to be treated,
b) providing an endoscopy tube having;
   i) a steering means,
   ii) an imaging means disposed at the distal end of the endoscopy tube, and
   iii) an illumination means disposed at the distal end of the endoscopy tube,
c) inserting the distal end of the end of the endoscopy tube within the second lumen of the tubular member at the open proximal end,
d) advancing the distal end of the endoscopy tube within the second lumen toward the distal end of the second lumen to dispose the imaging and illumination means adjacent to the optically transparent window for illuminating and obtaining images of tissues exterior to the tubular member and the tubular member covers the endoscopy tube, wherein said step of advancing provides a covered endoscopy tube,
e) inserting the covered endoscopy tube in a body cavity of a patient,
f) performing a treatment procedure that includes applying a quantity of liquid freezing agent to an area to be treated and obtaining images of the area to be treated at least after the treatment is performed,
g) removing the covered endoscopy tube from the body cavity,
h) removing the tubular member from the endoscopy tube,
i) disposing of the tubular member.

6. A method of using an endoscopy tube according to claim 5 wherein the covered
endoscopy tube is inserted into a body cavity of a patient from the nasal cavity of the patient.

7. The method of using an endoscopy tube according to claim 6 in which the body
cavity is the esophagus.

* * * * *